US007919456B2

(12) United States Patent
Ghosh

(10) Patent No.: US 7,919,456 B2
(45) Date of Patent: Apr. 5, 2011

(54) CONNECTIVE TISSUE DERIVED POLYPEPTIDES

(75) Inventor: Peter Ghosh, Fairlight (AU)

(73) Assignee: Proteobioactives Pty Ltd., Brookdale, New South Wales (AU)

(*) Notice: Subject to any disclaimer, the term of this patent is extended or adjusted under 35 U.S.C. 154(b) by 511 days.

(21) Appl. No.: 10/560,790

(22) PCT Filed: Jun. 17, 2004

(86) PCT No.: PCT/AU2004/000788
§ 371 (c)(1),
(2), (4) Date: Dec. 15, 2005

(87) PCT Pub. No.: WO2004/110475
PCT Pub. Date: Dec. 23, 2004

(65) Prior Publication Data
US 2007/0105763 A1    May 10, 2007

(30) Foreign Application Priority Data

Jun. 17, 2003  (AU) .............................. 2003903037

(51) Int. Cl.
C07K 14/00    (2006.01)
(52) U.S. Cl. .......................................... 514/2; 530/350
(58) Field of Classification Search .................. 530/350; 514/2
See application file for complete search history.

(56) References Cited

U.S. PATENT DOCUMENTS

| 5,364,845 | A | 11/1994 | Henderson |
| 5,399,347 | A | 3/1995 | Trentham et al. |
| 5,925,736 | A | 7/1999 | Neff et al. |
| 6,025,327 | A | 2/2000 | Alkayali |
| 6,127,523 | A | 10/2000 | Brewton et al. |

FOREIGN PATENT DOCUMENTS

| WO | 90/08195 | * | 7/1990 |
| WO | WO 01/93831 | | 12/2001 |
| WO | WO 01/93833 | | 12/2001 |
| WO | WO 03/062279 | | 7/2003 |

OTHER PUBLICATIONS

Vaughan-Thomas et al. 2001; EMBL AF419343.*
Lu et al., "Different Therapeutic and Bystander Effects by Intranasal Administration of Homologous Type II and Type IX Collagens on the Collagen-Induced Arthritis and Pristane-Induced Arthritis in Rats", Clinical Immunology (1999); 90(1): 119-127.
Myers et al., "Immunogenicity of Recombinant Type IX Collagen in Murine Collagen-Induced Arthritis", Arthritis & Rheumatism (2002); 46(4): 1086-1093.
Vasios et al., "Cartilage Type IX Collagen-Proteoglycan Contains a Large Amino-terminal Globular Domain Encoded by Multiple Exons", The Journal of Biological Chemistry (1988); 263(5): 2324-2329.
Barnett et al., "A pilot trial of oral type II collagen in the treatment of juvenile rheumatoid arthritis." Arthritits Rheum. (1996) 39(4): 623-628.
Chen et al., "Peripheral deletion of antigen-reactive T cells in oral tolerance," Nature (1995) 376: 177-180.
Cremer et al., "The cartilage collagens: a review of their structure, organization, and role in the pathogenesis of experimental arthritis in animals and in human rheumatic disease," J. Mol. Med. (1998) 76: 275-288.
Eyre et al., "Collagen type IX: evidence for covalent linkages to type II collagen in cartilage," FEB (1987) vol. 200, No. 2, 337-341.
Faria et al., "Oral Tolerance: Mechanisms and Therapeutic Applications," Advances in Immunology (1999) vol. 73, 153-264.
Holden et al., "Cartilage Oligomeric Matrix Protein Interacts with Type IX Collagen, and Disruptions to These Interactions Identify a Pathogenetic Mechanism in a Bone Dysplasia Family," The Journal of Biological Chemistry (2001)vol. 276, No. 8, 6046-6055.
J. Kuby, "Immunology, Second Edition" WH Freeman and Company (1994) Chapter 16, pp. 369-391.
Maciewicz et al., "A comparison of four cathepsins (B, L, N and S) with collagenolytic activity from rabbit spleen," Biochem J. (1988) 256, 433-440.
Needleman et al., "A General Method Applicable to the Search for Similarities in the Amino Acide Sequence of Two Proteins," J. Mol. Biol. (1970) 48, 443-453.
Pihlajamaa et al., "Characterization of Recombinanat Human Type IX Collagen, association of α chains into homotrimeric and heterotrimeric molecules," The Journal of Biological Chemistry (1999) vol. 274, No. 32, 22464-22468.
Smith et al., "Measurement of protein using bicinchoninic acid." Anal Biochem. (1985) 150(1): 76-85.
Smith et al., "Effects of Calcium Pentosan Polysulfate on Joint Inflammation and Pouch Fluid Levels of Leukocytes, Nitric Oxide, and Interleukin-6 in a Rat Model of Arthritis," Current Therapeutic Research (1999) vol. 60, No. 11, 561-576.
Stegemann et al., "Determination of Hydroxyproline," Clinica Chimica Acta (1967) 18: 267-273.
Trentham et al., "Effects of oral administration of type II collagen on rheumatoid arthritis." Science (1993) 261(5129): 1727-1730.
Weiner et al., "Oral tolerance and the treatment of rheumatoid arthritis," Springer Seminars in Immunopathology (1998) 20: 289-308.
Fassler et al. "Mice lacking α1 (IX) collagen develop noninflammatory degenerative joint disease." Proc. Natl. Acad. Sci. vol. 91. 1994. pp. 5070-5074.
Haimes et al. "Overexpression of the NC$_4$ domain of type IX collagen induces osteoarthritisu in mice." Inflamm Res. vol. 44. Supplement. 2. 1995. pp. 127-128.
Kojima et al. "Early Degradation of Type IX and Type II Collagen with the Onset of Experimental Inflammatory Arthritis." Arthritis & Rheumatism. vol. 44, No. 1 2001. pp. 120-127.
European Office Action dated Oct. 20, 2009.

* cited by examiner

Primary Examiner — Karen Cochrane Carlson
(74) Attorney, Agent, or Firm — Merchant & Gould P.C.

(57) ABSTRACT

The present invention relates to compositions comprising one or more connective tissue derived polypeptides having a molecular weight of less than 30,000 Da that are capable of tolerising individuals to antigenic components of cartilage and prevent the appearance of and/or treat symptoms of arthritis and other musculoskeletal degenerative conditions. The present invention provides methods for recovering polypeptides having a molecular weight of less than 30,000 Da from connective tissue and having anti-arthritic or anti-inflammatory activity. The present invention further relates to compositions comprising a polypeptide containing an NC4 domain of collagen type IX alpha 1 chain or fragment thereof, having a molecular weight of less than 30,000 Da, where the polypeptide is capable of tolerising individuals to antigenic components of cartilage, preventing the appearance of arthritic symptoms, and/or treating the symptoms of arthritis.

24 Claims, 7 Drawing Sheets

Fractionation of Peptacans into GAG-peptides and Polypeptides

CONNECTIVE TISSUE DERIVED POLYPEPTIDES

This application is the National Stage Application of International Application No. PCT/DK2004/000788, filed on Jun. 17, 2004, which claims priority to Application No. 2003 90 3037, filed on Jun. 17, 2003 in Denmark.

TECHNICAL FIELD

The present invention relates to methods for treating and preventing arthritis and other degenerative diseases and to inducing tolerance in an individual to an antigenic component of cartilage, the present invention also relates to novel methods for preparing and recovering connective tissue derived polypeptides, their uses in methods of treatment, and protection of connective tissues in arthritis and other degenerative diseases.

BACKGROUND OF THE INVENTION

1. General

As used in the specification and claims, the singular form "a," "an" and "the" include plural references unless the context clearly dictates otherwise. For example, the term "a fungal pathogen" includes a plurality of fungal pathogens, including mixtures thereof.

As used herein the term "derived from" shall be taken to indicate that a specified integer are obtained from a particular source albeit not necessarily directly from that source.

A "composition" is intended to mean a combination of active agent and another compound or composition, inert (for example, a detectable agent or label) or active, such as an adjuvant.

Unless the context requires otherwise or specifically stated to the contrary, integers, steps, or elements of the invention recited herein as singular integers, steps or elements clearly encompass both singular and plural forms of the recited integers, steps or elements.

The embodiments of the invention described herein with respect to any single embodiment shall be taken to apply mutatis mutandis to any other embodiment of the invention described herein.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein. Functionally equivalent products, compositions and methods are clearly within the scope of the invention, as described herein.

The present invention is performed without undue experimentation using, unless otherwise indicated, conventional techniques of molecular biology, microbiology, virology, recombining DNA technology, peptide synthesis in solution, solid phase peptide synthesis, and immunology. Such procedures are described, for example, in the following texts that are incorporated herein by reference:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135151;
4. Nucleic Acid Hybridization: A Practical Approach (B. D. Hames & S. J. Higgins, eds., 1985) IRL Press, Oxford, whole of text;
5. Perbal, B., A Practical Guide to Molecular Cloning (1984);
6. Wiinsch, E., ed. (1974) Synthese von Peptiden in Houben-Weyls Metoden der Organischen Chemie (Miiler, E., ed.), vol. 15, 4th edn., Parts 1 and 2, 30 Thieme, Stuttgart.
7. Handbook of Experimental Immunology, Vols. I-IV (D. M. Weir and C. C. Blackwell, eds., 1986, Blackwell Scientific Publications) Bibliographic details of the publications referred to in this specification are collected at the end of the description 2. Background art Diseases of the musculoskeletal system such as rheumatoid arthritis (RA), osteoarthritis (OA), disc degeneration (DD), and osteoporosis (OP) are a major cause of morbidity throughout the world. These diseases have a substantial influence on health and quality of life and inflict an enormous cost on health systems.

The aetiology of OA is considered to be multi-factorial with ageing, mechanical, hormonal and genetic factors all contributing to varying degrees. OA emerges as a clinical syndrome when these etiological determinants result in sufficient joint tissue damage to cause synovial inflammation and the appearance of the symptoms of pain and impairment of function.

RA is thought to arise as a consequence of extrinsic and/or intrinsic triggering of an autoimmune response in genetically susceptible individuals. The aggressive inflammation initiated in the joints of RA patients by the activation of their immune system is manifest by the release of pro-inflammatory cytokines, proteinases and free radicals. All of these mediators have the ability to promote the destruction of cartilage, bone and other intra-articular joint tissues leading to further impairment of joint function and progression of the disease. While both OA and RA show common pathological features of cartilage destruction and synovial inflammation, the origins and temporal history of these events are clearly distinct. Nevertheless, destruction of joint cartilage is common to both OA and RA and there is now strong evidence that the breakdown and release of the matrix components from cartilage play a significant role in the chronicity of these diseases.

Cartilage may be considered as an anisotropic biomaterial composed essentially of a three-dimensional fibrous network of type II collagen fibrils copolymerised with types IX and XI collagens embedded in a proteoglycan (PG) rich hydrated extracellular matrix. Type II collagen accounts for over 90% of the total collagen of adult cartilage while the type IX content is only 1-2%.

Type IX collagen is a heteropolymer consisting of three genetically distinct alpha chains, α1(IX), α2 (IX) and α3 (IX) whose molecular structure and amino acid sequences have been described (Pihlajamaa T, et al. Characterisation of recombinant human type IX collagen, association of α chains into homotrimeric and heterotrimeric molecules. J Biol Chem, 274: 22464-22468, 1999)(U.S. Pat. No. 6,127,523, Oct. 3, 2000). The type IX α-chains contain 3 triple-helical domains, COL1, COL2 and COL3 and four non-collagenous domains, NC1, NC2, NC3 and NC4. The NC1 and NC3 regions contain cysteine residues that can form intramolecular disulfide linkages between the α-chains. Only the α1(IX) chain contains a NC4 domain (see FIG. 1) and the sequence from chick sternia has been shown to consist of 243 amino acid residues with a calculated molecular mass of 27,139 Da and overall positive charge (Vasios G, Nishimura I, Konomi H, van der Rest M, Cartilage Type IX collagen-proteoglycan contains a large amino-terminal globular domain encoded by multiple exons. J Biol Chem 263: 2324-2329, 1988).

The type IX collagen heteropolymer is linear except that the NC3 domain acts like a hinge allowing the NC4 region of the α1 chain to project away from the other chains. Interestingly, a single chondroitin sulfate chain is attached to the NC3 domain.

Although only a minor component of cartilage, type IX collagen provides an important role in maintaining the type II collagen fibrous network assembly which is essential for the optimum physical function of this weight-bearing tissue. Type IX collagen resides on the surface of the type II collagen fibrils to which it is covalently linked via, at least 2 trivalent pyridinoline cross-links, particularly at sites where the type II fibril network intersects. By cross-linking the type II collagen fibrils type IX collagen would appear to constrain the expansion caused by the imbibition of water molecules attracted into the tissue by the trapped negatively charged proteoglycan (PG) aggregates (referred to herein as aggrecans). In addition the positively charge centres on the globular NC4 domain also provides a potential binding site for the polyanionic aggrecans.

The aggrecans of cartilage are macro-molecular aggregates of PG subunits which are non-covalently attached along the length of a hyaluronic acid chain. Each aggrecan may contain 20-50 PG subunits and their interaction with the HA backbone is stabilised by ternary interactions with link protein. The PG subunits consist of a protein core to which up to 100 GAG chains are covalently linked. The major GAG substituents of the PGs are the chondroitin sulfates (ChS) and keratan sulfate.

In addition to the collagens and proteoglycans, cartilage also contains a large number of non-collagenous proteins, the most abundant being cartilage oligomeric protein (COMP), cartilage matrix protein (CMP), and thrombospondin. COMP is considered to be a key structural component of the cartilage matrix since it interacts with type IX collagen and plays a role in the development and assembly of type II collagen fibrils (Holden P, et al. Cartilage oligomericmatrix protein interacts with type IX collagen and disruptions to these interactions identify a pathogenic mechanism in a bone displasia familly. J Biol Chem, 276: 6046-6055, 2001). In the early stages of arthritis when cartilage breakdown is increased, PGs, type IX collagen and COMP fragments are some of the first matrix components to be released into synovial fluid by the action of endogenous proteinases. These products of cartilage breakdown have been shown to be antigenic and can induce an inflammatory response within arthritic joints thereby contributing to the rate of disease progression.

In arthritic diseases, the excessive breakdown of cartilage and bone and the concomitant elicitation of an inflammatory reaction provoked by the release of autoantigens are responsible for their chronicity. However, there is accumulating evidence to indicate that these matrix molecules could also be responsible for the initiation of joint diseases by acting as autoantigens. Indeed, systemic administration of type II collagen or other matrix components together with adjuvants to laboratory animals have been used to produce animal models of arthritic disease (Creamer M A, Rosloniec E F, Kang A H. The cartilage collagens: a review of their structure, organization and role in the pathogenesis of experimental arthritis in animals and human rheumatic disease, *J Mol Med,* 76: 275-288, 1998).

In the case of cartilage collagens, this knowledge has led to the development of means of treating rheumatic diseases by using the concept of oral tolerisation (Weiner, H L, Komagata Y. Oral tolerance and the treatment of Rheumatoid Arthritis. Seminars Immunopath, 20: 289-308, 1998). Thus it has been shown that suppression of type II collagen-induced arthritis in animal models can be achieved by oral administration of low doses of type II collagen. Oral tolerisation of arthritic patients by administration of type II collagen has also been shown to be effective clinically and therapeutic effects have been reported with small (less than 100 mg) daily doses of type II collagen antigens. Studies using rheumatoid and juvenile rheumatoid arthritis patients confirmed the efficacy and safety of low daily oral doses of type II collagen derived from chick sterna (Trentham D, et al. Effects of oral administration of type II collagen on rheumatoid arthritis. Science, 261: 1727-1730, 1993) (Barnett et al, A pilot study of oral type II collagen in the treatment of juvenile rheumatoid arthritis. Arthritis. Rheum. 39:623-628, 1996). Other studies have indicated that cartilage collagens obtained from bovine sources were less effective than those prepared from chick cartilage.

Unfortunately, some studies have found that high doses of type II collagen may in fact exacerbate disease since, as already indicated, this cartilage derived antigen is also an arthritogen and it is difficult to accurately determine how much of this antigen would be effective or detrimental to the arthritic process. With regard to other cartilage collagens types X, XI are arthritogenic, while type IX collagen has been reported to be not as effective as type II collagen as a tolerant in some animal arthritis models (Lu S et al, Different therapeutic and bystander effects by intranasal administration of homologous type II and type IX collagens on the collagen-induced arthritis and Pristane-induced arthritis in rats. Clin Immunol. 90:119-127, 1999).

In another study using recombinantly produced in-tact native type IX collagen it was found that when it was given orally to B10 congenic mice this collagen was able to ameliorate the arthritis produced by prior inoculation with type II collagen (collagen induced arthritis, CIA). The recombinant type IX collagen was also tested for immunogenicity in other murine models and unlike type II collagen, it failed to induce overt arthritis in mice immunized with this protein (Myers L K et al, Immunogenicity of recombinant Type IX collagen in murine collagen-induced arthritis. Arthritis Rheum. 46:1086-1093, 2002).

The discrepancy between the Lu et al (1999) and Myers et al (2002) may be explained by differences in the purity and molecular size of the type IX collagen preparations. Recombinant technology is considered the only means of obtaining pure native type IX collagen since very little can be extracted from the cartilage matrix without using proteolysis as it is covalently bound to the type II collagen fibrils. The most common proteinase used to extract type IX collagen from cartilages is pepsin which is a commercial preparation generally derived from porcine stomach mucosa. Pepsin is not present in cartilage. This enzyme hydrolyses the non-collagenous domains of the type IX molecule releasing the native COL1, COL2, and COL3 triple helical segments which are isolated from the mixture by precipitation leaving the partially degraded non-helical NC domains in solution.

The endogenous proteinases responsible for the normal turnover of type IX collagen in cartilaginous tissues are presently unknown. However, the matrix metalloproteinase (MMP) family, the serine proteinases and cysteine proteinases are all known to degrade type IX collagen in vitro in both the helical (COL) and non-helical (NC) domains.

SUMMARY OF INVENTION

In work leading up to the present invention, the inventor sought to recover connective tissue derived polypeptides having anti-arthritic or anti-inflammatory activity. The inventor found that polypeptides produced by autolysis of connective tissue and having a molecular weight of less than 30,000 Da had anti-arthritic or anti-inflammatory activity.

The inventor also found that administration of a composition comprising one or more connective tissue derived polypeptides having a molecular weight of less than 30,000 Da, tolerised individuals to antigenic components of cartilage and prevented the appearance of symptoms of arthritis.

Analysis of the polypeptides using proteomic techniques showed that fragments of the polypeptide produced by their tryptic digestion had strong identity with the NC4 domain of collagen type IX alpha 1 chain.

Accordingly, the present invention relates to the use of a polypeptide comprising a collagen type IX alpha 1 chain NC4 domain or biologically active fragment thereof having anti-arthritic or anti-inflammatory activity for the treatment or prevention of arthritis or other degenerative disease of the musculoskeletal system in an individual.

In a first aspect the invention provides a pharmaceutical composition for treating or preventing arthritis or other degenerative disease in an individual, said composition comprising a polypeptide comprising a collagen type IX alpha 1 chain NC4 domain or biologically active fragment thereof having anti-arthritic or anti-inflammatory activity in combination with a pharmaceutically acceptable carrier. In a preferred embodiment, the polypeptide has a molecular weight of less than 30,000 Da and/or an amino acid length of less than 250 amino acids. In a further preferred embodiment, the polypeptide or biologically active fragment thereof is derived from a mammal.

In another aspect the invention provides a pharmaceutical composition for inducing tolerance in an individual to at least one antigenic component of cartilage, said composition comprising a polypeptide comprising collagen type IX alpha 1 chain NC4 domain or biologically active fragment thereof having anti-arthritic or anti-inflammatory activity in combination with a pharmaceutically acceptable carrier. In a preferred embodiment the collagen type IX alpha 1 chain NC4 domain polypeptide has a molecular weight of less than 30,000 Da or an amino acid length of less than 250 amino acids.

In one example, the collagen type IX alpha 1 chain NC4 domain comprises
(i) an amino acid sequence as provided in SEQ ID NO 1, SEQ ID NO 14, SEQ ID NO 16, or SEQ ID NO 18,
(ii) an amino acid sequence which is at least 70% identical to either SEQ ID NO 1, SEQ ID NO 14, SEQ ID NO 16, or SEQ ID NO 18, or
(iii) a biologically active fragment of (i) or (ii).

Preferably, the collagen type IX alpha 1 chain NC4 domain comprises an amino acid sequence which is at least 75%, preferably 80%, 85%, 90% or 95% identical to any one of SEQ ID NO 1, SEQ ID NO 14, SEQ ID NO 16, or SEQ ID NO 18.

In one example, the collagen type IX alpha 1 chain NC4 domain comprises:
(i) an amino acid sequence as provided in residues 21-182 of SEQ ID NO 1; residues 60-181 of SEQ ID NO 1; residues 72-181 of SEQ ID NO 1, residues 98-182 of SEQ ID NO 1, or residues 123-182 of SEQ ID NO 1; or
(ii) an amino acid sequence as provided in residues Ala1-Arg245 of SEQ ID NO 14; residues Pro6-Arg245 of SEQ ID NO 14, residues Pro6-Asp192 of SEQ ID NO 14, residues Pro6-Arg186 of SEQ ID NO 14, residues Pro6-Pro185 of SEQ ID NO 14, residues Pro6-Arg73 of SEQ ID NO 14, or residues Pro85-Pro185 of SEQ ID NO 14.

In another example, the collagen type IX alpha 1 chain NC4 domain comprises at least one of SEQ ID NOs 2-11.

In a preferred embodiment, inducing tolerance in the individual prevents at least one symptom of arthritis or other musculoskeletal degenerative condition in the individual.

As used herein to "prevent at least one symptom" refers to defending against or inhibiting a symptom, delaying the appearance of a symptom, reducing the severity of the development of a symptom, and/or reducing the number or type of symptoms suffered by an individual, as compared to not administering a pharmaceutical composition comprising a polypeptide of the invention. Accordingly, throughout this description, it will be understood that any clinically or statistically significant attenuation of even one symptom of a musculoskeletal degenerative condition pursuant to the treatment according to the present invention is within the scope of the invention.

The present invention also provides a method of inducing tolerance in an individual to at least one antigenic component of cartilage comprising administering the individual with an effective amount of the pharmaceutical composition according to the first aspect of the invention.

Preferably the method of inducing tolerance in the individual prevents the onset of the musculoskeletal degenerative condition.

Accordingly, the invention provides a method for preventing a musculoskeletal degenerative condition in an individual comprising administering a pharmaceutically effective amount of a composition according to the first aspect to the individual.

Further, the invention provides a method for preventing an autoimmune response to at least one antigenic component of cartilage comprising administering a composition according to the first aspect of the individual.

In related aspects, the invention further provides for use of a polypeptide comprising a collagen type IX alpha 1 chain NC4 domain or biologically active fragment having anti-arthritic or anti-inflammatory activity in combination with a pharmaceutically acceptable carrier in the manufacture of a medicament for inducing tolerance to at least one antigenic component of cartilage or for preventing a musculoskeletal degenerative condition in an individual.

Preferably, the pharmaceutical composition of the present invention is one which prevents at least one symptom of arthritis, such as for example inflammation, joint tenderness, joint swelling, joint stiffness, restricted mobility, or strength reduction, when administered to a naive individual.

In one example, the individual is a naive individual. By "naïve individual" is meant that preferably the individual does not present two or more symptoms of a musculoskeletal degenerative condition, more preferably the individual does not present a symptom of a musculoskeletal degenerative condition. This may be prior to or during or post the course of a musculoskeletal disease.

In a further aspect, the present invention provides methods for recovering polypeptides having a molecular weight of less than 30,000 Da from connective tissue wherein connective tissue particles are subjected to autolysis in the presence of an autolysis medium such that a mixture of glycosaminoglycan peptides and polypeptides are released from the connective tissue particles into the autolysis medium. The process of inducing autolysis has previously been described in PCT/AU03/00061 (in the name of the Applicant), which is incorporated herein by reference. According to the invention, polypeptides are recovered from the medium and are separated according to size. The invention also provides methods for separating and identifying the recovered polypeptides according to their size and charge.

Accordingly, in one example the method for preparing a polypeptide having anti-arthritic or anti-inflammatory activity comprises isolating a mixture comprising a GAG-peptide and a polypeptide having a molecular weight of less than 30,000 Da by autolysis from connective tissue, separating the GAG-peptide from the polypeptide, and recovering the polypeptide.

In a related example, the present invention provides a method for preparing a polypeptide having anti-arthritic or anti-inflammatory activity, the method comprising
(i) incubating a connective tissue in an autolysis medium that provides a buffered pH range of between about pH 2.5 and about pH 8.5 for a time and under conditions sufficient to release a GAG-peptide and a polypeptide having a molecular weight of less than 30,000 Da,
(ii) recovering a mixture comprising the GAG-peptide and polypeptide from the autolysis medium;
(iii) separating the polypeptide from the GAG-peptide; and
(iv) recovering the polypeptide having a molecular weight of less than 30,000 Da.

Any well known techniques such as for example, chromatography, ion exchange techniques, gel filtration (eg. diafiltration or ultrafiltration), gel electrophoresis (eg. one dimensional or two dimensional) or any other method of separating and/or recovering polypeptides according to their size and molecular weight, or combination thereof, can be used to recover the polypeptide from the mixture.

A combination of the same or similar techniques may be used and may be repeated. In this way, fractions of polypeptides of different molecular weight ranges may be obtained and individual polypeptides can also be recovered.

Polypeptides recovered by the method of the invention are connective tissue derived polypeptides. The present invention clearly contemplates that the recovered polypeptides may comprise mixtures of polypeptides or individual polypeptides.

The inventor has found that the recovered polypeptides and mixtures thereof have enhanced and/or different pharmacological activities to the GAG-peptide/polypeptide mixture. The polypeptides according to the present invention are those connective-tissue derived polypeptides having anti-arthritic or anti-inflammatory activity. In one embodiment, a polypeptide of the invention reduces rear paw inflammation in rats with collagen induced arthritis. In another embodiment, a polypeptide of the invention decreases tail inflammation in rats with collagen induced arthritis. In another embodiment, a polypeptide of the invention decreases fore paw inflammation in rats with collagen induced arthritis. In yet another embodiment, a polypeptide of the invention decreases weight loss in rats with collagen induced arthritis.

Accordingly, another example of the present invention provides a connective tissue derived polypeptide, having a molecular weight of less than 30,000 Da which is obtainable by the method of the invention, and having anti-arthritic or anti-inflammatory activity.

For example, the invention provides a connective tissue derived polypeptide having a molecular weight of less than 30,000 Da which is obtainable by:
(i) incubating a connective tissue in an autolysis medium that provides a buffered pH range of between about pH 2.5 and about pH 8.5 for a time and under conditions sufficient to release a GAG-peptide and a polypeptide having a molecular weight of less than 30,000 Da,
(ii) recovering a mixture comprising the GAG-peptide and polypeptide from the autolysis medium;
(iii) separating the polypeptide from the GAG-peptide; and
(iv) recovering the polypeptide having a molecular weight of less than 30,000 Da.

In one example, the recovered polypeptide comprises a non-collagenous region-4 (NC4) of the collagen type IX al chain, or biologically active fragment thereof.

The effects observed for the polypeptides of the invention on rats with collagen induced arthritis also provide application for the polypeptides in the treatment, protection and restoration of connective tissues in inflammatory and degenerative tissue diseases such as rheumatoid arthritis and osteoarthritis in all animals. Preferably, the polypeptides of the present invention prevent antigen driven autoimmune diseases in animals. In another preferred embodiment, polypeptides of the invention reduce symptoms associated with antigen driven autoimmune diseases in animals.

Accordingly, it is to be understood that the forgoing examples apply mutatis mutandis to each and every aspect of the invention.

Accordingly, the invention provides a pharmaceutical composition for treating or preventing arthritis or other musculoskeletal degenerative disease in an individual, said composition comprising one or more connective tissue derived polypeptides having anti-arthritic or anti-inflammatory, wherein said polypeptide is obtainable by a method comprising isolating a mixture comprising a GAG-peptide and a polypeptide having a molecular weight of less than 30,000 Da by autolysis from connective tissue, separating the GAG-peptide from the polypeptide, and recovering the polypeptide.

The invention also provides a pharmaceutical composition for inducing tolerance in an individual to at least one antigenic component of cartilage, said composition comprising one or more connective tissue derived polypeptides having anti-arthritic or anti-inflammatory, wherein said polypeptide is obtainable by a method comprising isolating a mixture comprising a GAG-peptide and a polypeptide having a molecular weight of less than 30,000 Da by autolysis from connective tissue, separating the GAG-peptide from the polypeptide, and recovering the polypeptide having a molecular weight of less than 30,000 Da.

Preferably, inducing tolerance in the individual prevents at least one symptom of a musculoskeletal degenerative disease in the individual.

In another example, the present invention provides a method for preventing a musculoskeletal degenerative condition in an individual comprising administering the individual with an effective amount of a pharmaceutical composition comprising one or more connective tissue derived polypeptides having anti-arthritic or anti-inflammatory, wherein said polypeptide is obtainable by a method comprising isolating a mixture comprising a GAG-peptide and a polypeptide having a molecular weight of less than 30,000 Da by autolysis from connective tissue, separating the GAG-peptide from the polypeptide, and recovering the polypeptide having a molecular weight of less than 30,000 Da.

In another example, the present invention provides a method for preventing autoimmune response in an individual to at least one antigenic component of cartilage comprising administering the individual with an effective amount of a pharmaceutical composition comprising one or more connective tissue derived polypeptides having anti-arthritic or anti-inflammatory, wherein said polypeptide is obtainable by a method comprising isolating a mixture comprising a GAG-peptide and a polypeptide having a molecular weight of less than 30,000 Da by autolysis from connective tissue, separating the GAG-peptide from the polypeptide, and recovering the polypeptide having a molecular weight of less than 30,000 Da.

The present invention further provides a method of inducing cartilage formation in an individual, comprising administering to the individual an effective amount of a connective tissue derived polypeptide according to the invention and having anti-arthritic or anti-inflammatory activity, wherein said polypeptide is obtainable by a method comprising isolating a mixture comprising a GAG-peptide and a polypeptide having a molecular weight of less than 30,000 Da by autolysis from connective tissue, separating the GAG-peptide from the polypeptide, and recovering the polypeptide having a molecular weight of less than 30,000 Da.

In other related examples, the present invention provides for use of one or more connective tissue derived polypeptides having anti-arthritic or anti-inflammatory, in the preparation of a medicament for the treatment or prevention of arthritis or other musculoskeletal disease in a subject, wherein said polypeptide is obtainable by the method comprising isolating a mixture comprising a GAG-peptide and a polypeptide having a molecular weight of less than 30,000 Da by autolysis from connective tissue, separating the GAG-peptide from the polypeptide, and recovering the polypeptide.

In one example the invention provides for the use of one or more connective tissue derived polypeptides having anti-arthritic or anti-inflammatory, in the preparation of a medicament for tolerising an individual to at least one antigenic component of cartilage, wherein said polypeptide is obtainable by a method comprising isolating a mixture comprising a GAG-peptide and a polypeptide having a molecular weight of less than 30,000 Da by autolysis from connective tissue, separating the GAG-peptide from the polypeptide, and recovering the polypeptide having a molecular weight of less than 30,000 Da.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

DETAILED DESCRIPTION OF THE FIGURES

FIG. 1 is a schematic representation of the Human type IX collagen molecule showing the 3 α chains which constitute the heteropolymer and their collagenous (COL) and non-collagenous (NC) domains. The COL regions are triple helical while the NC domains are non-helical. Cysteine residues in the NC3 and NC1 Regions allow disulfide bond interactions. NC4 is only present on the α1(IX chain and is overall positively charged allowing it to interact with polyanionic glycosaminoglycans in the extracellular matrix. A single chondroitin sulfate chain is attached, via a serine residue, to the NC3 region of the α2(IX) chain in the native molecule.

Figure 2:
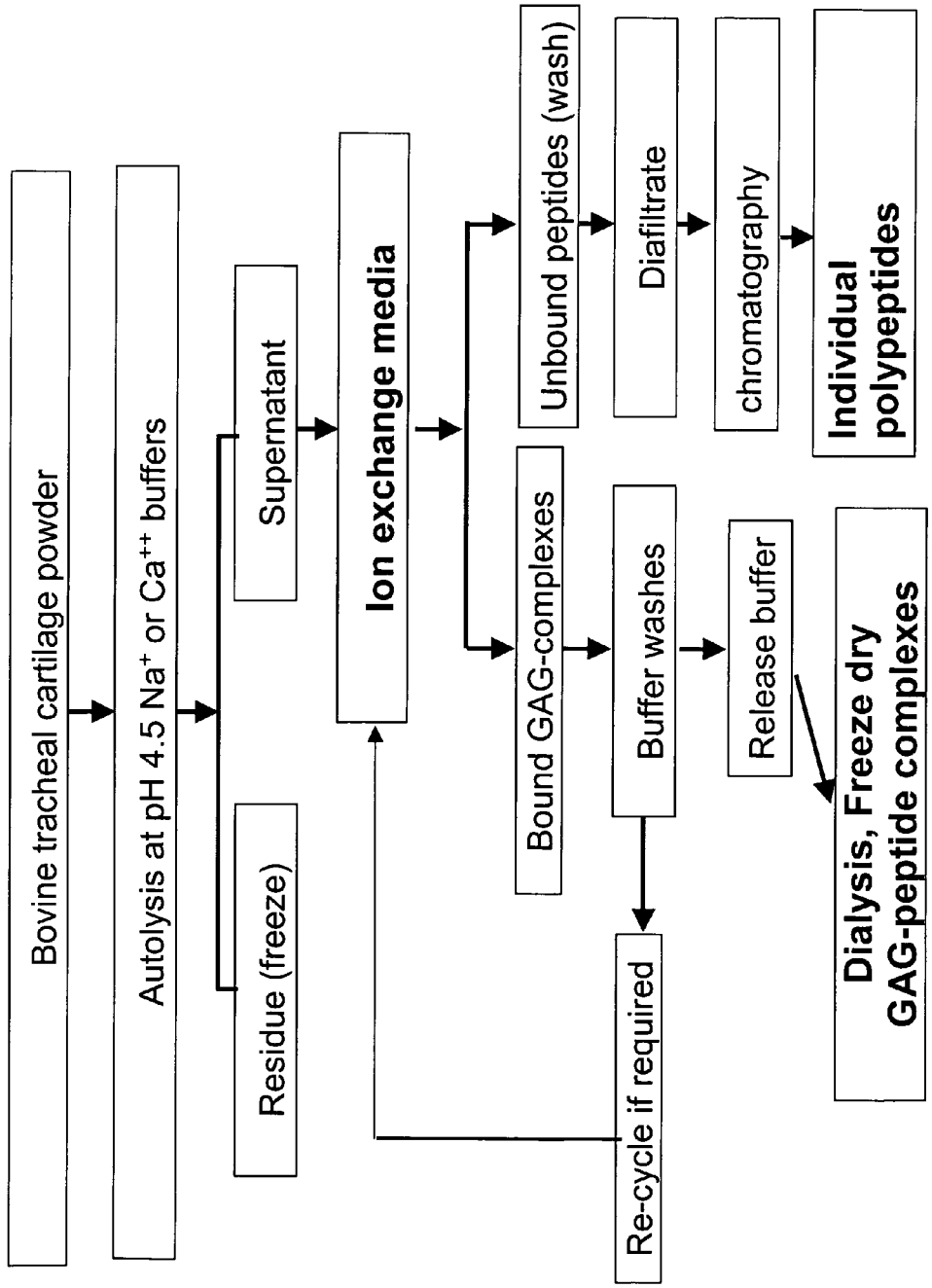
FIG. 2 is a schematic diagram of the methods used for the separation and sub-fractionation of the glycosaminoglycan peptide and polypeptide mixture (eg calcium peptacan (CaP)) into purified GAG-peptides and polypeptides using ion exchange media.
Figure 4:
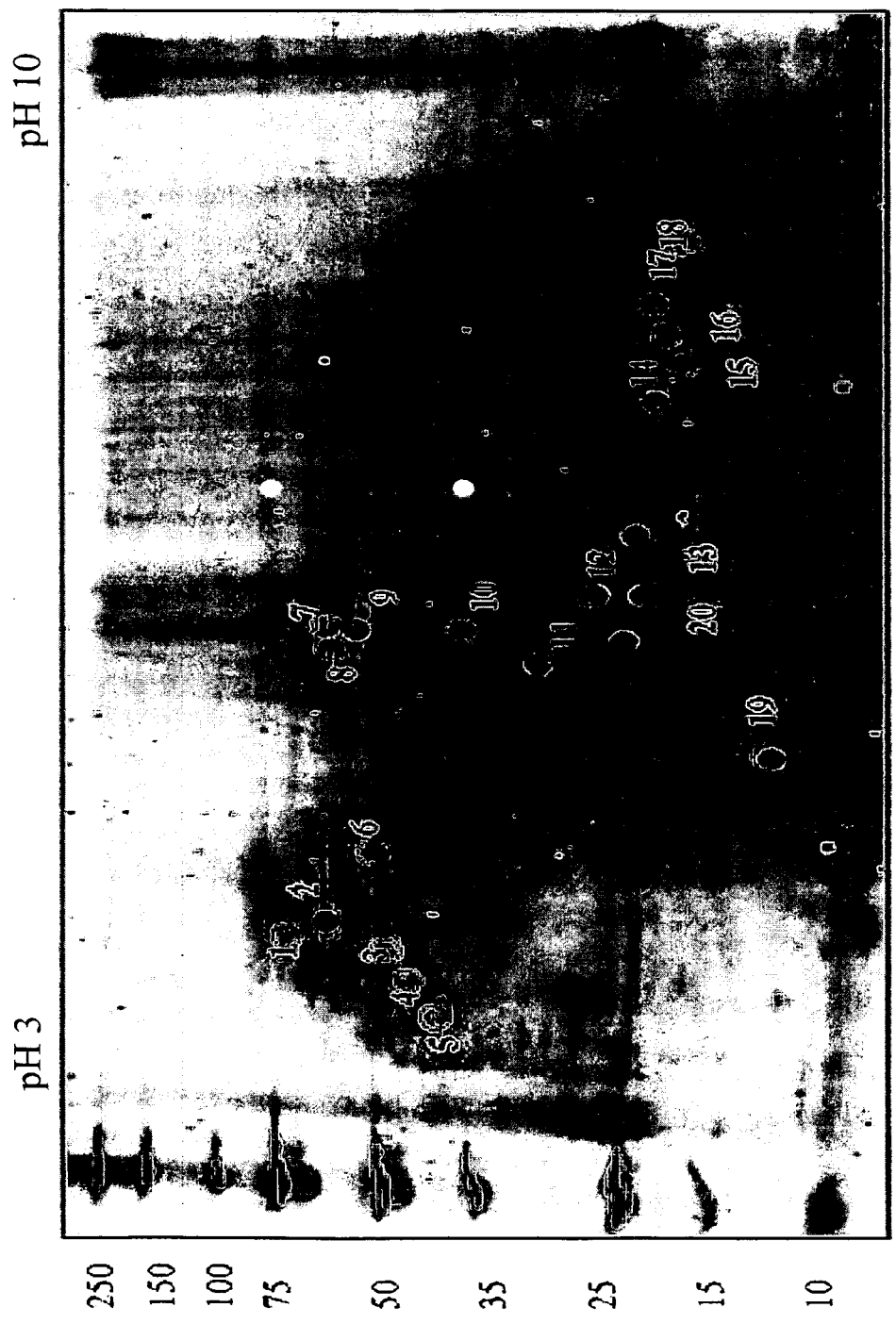

FIG. 4 is a photographic representation of the SDS-PAGE 2-D electrophoresis of the proteins/polypeptides isolated from the glycosaminoglycan-peptide and polypeptide mixture (CaP) using the ion-exchange schema shown in FIG. 2. The majority of the spots resolved by this procedure were isolated and subjected to trypsin digestion sequence analysis using Matrix Assisted Laser Desorption Ionisation mass spectrometry (MALDI-MS).

Figure 5:
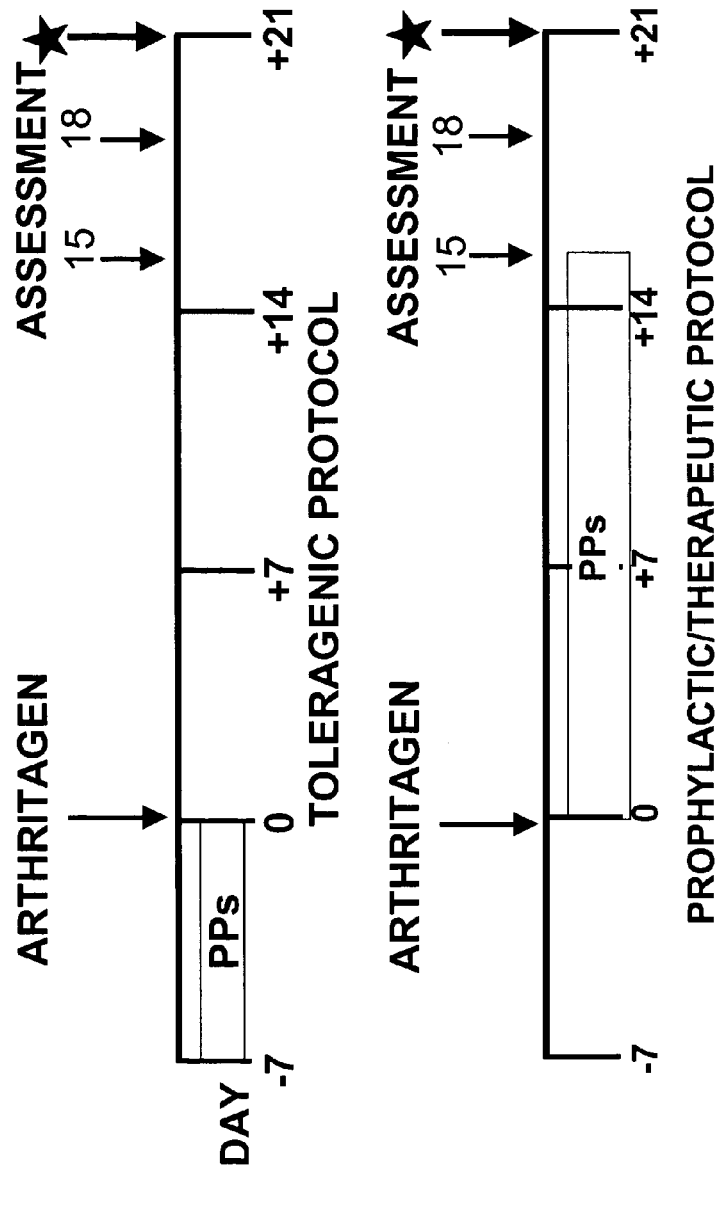

FIG. 5 is summary of the toleragenic and prophylactic/therapeutic protocols used to evaluate the antiarthritic effects of the polypeptides INR-195 and INR-126 in the rat collagen induced arthritis (CIA) model.

Figure 6:

FIG. 6 show representative photomicrographs of stained histological sections, prepared and stained using standard methods, of hind-paw joints from normal and the untreated rat collagen induced arthritis (CIA) model at day 18 showing the extent of inflammatory cell invasion and destruction of tendons, cartilage and bone.

Figure 7:
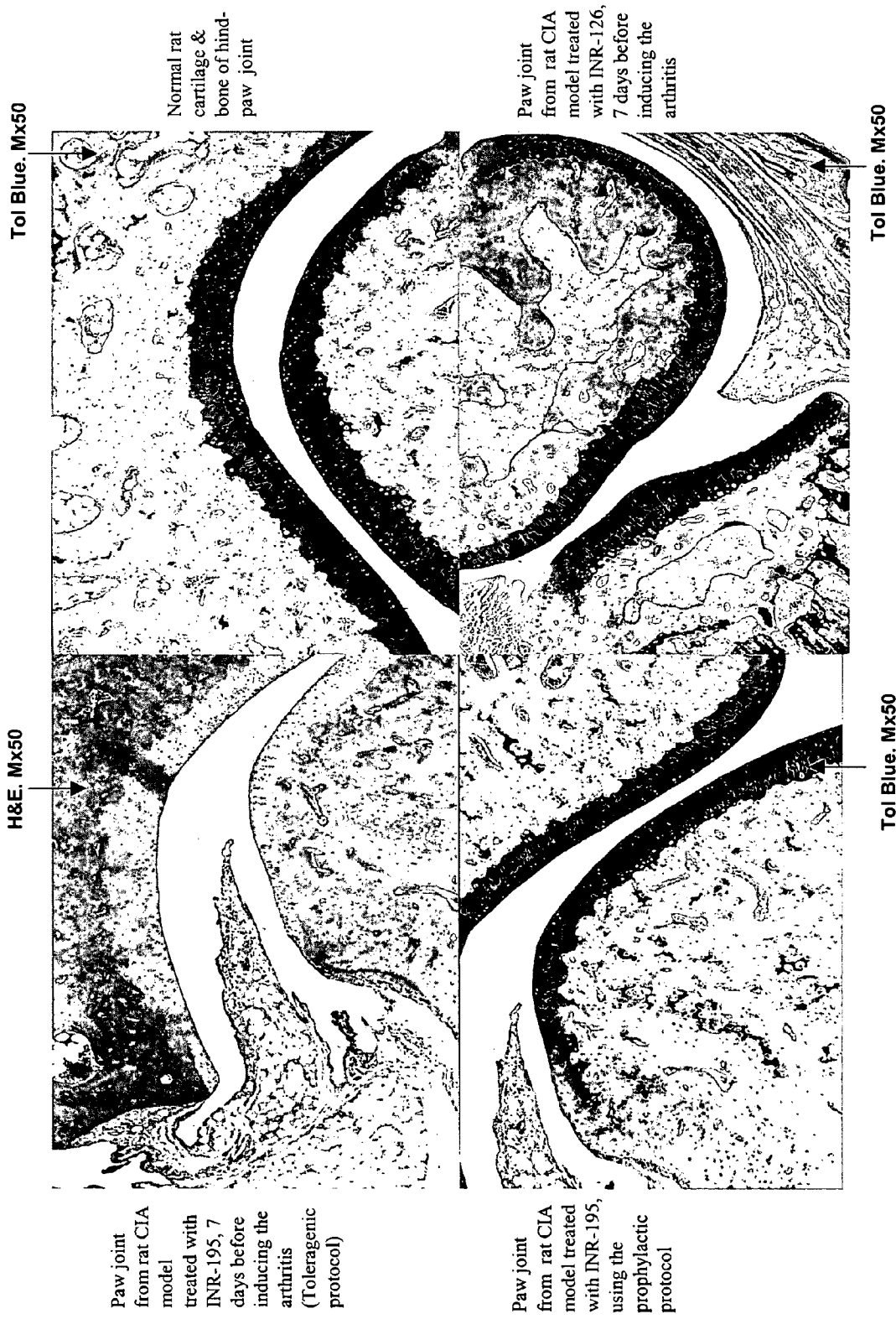

FIG. 7 shows representative photomicrographs of stained histological sections, prepared and stained using standard methods, of hind-paw joints from normal and the rat collagen induced arthritis (CIA) model at day 18 of animals treated orally with the polypeptides INR-126 (20 mg/kg) and INR195 (20 mg/kg) using the toleragenic or prophylactic/therapeutic protocols. Note the reduction of the inflammatory cell invasion and destruction of tendons, cartilage and bone compared to the untreated groups shown in FIG. 6.

DETAILED DESCRIPTION OF THE INVENTION

1. Autolysis

Connective tissue is an animal tissue that supports organs, fills the spaces between them, and forms tendons and ligaments. The term "tissue" as used herein refers to a group of similarly specialised cells that perform a common function. As used herein, tissue is intended to include an organ composed of a given tissue and to the cells, individually or collectively, that compose the tissue.

In one embodiment, the connective tissue is a cartilage. In another embodiment, the connective tissue is non-cartilage material eg. lung, skin, bone, ligament or tendon.

Preferably the cartilage is tracheal, articular, auricular, nasal, sternal, rib skeletal, or antler cartilage. Cartilage may, however, be any type of cartilage.

Connective tissue may be obtained from any animal having connective tissue.

In one embodiment, connective tissue is selected from any one of the following: human, bovine, ovine, porcine, equine, avian, cervine and piscine species. Preferably the connective tissue is bovine, ovine, porcine, cervine, shark or equine.

In one embodiment tissues from young animals are preferable eg a calf. In an alternate embodiment a more mature animal is preferred.

The connective tissue may be treated and washed as required by methods known in the art to remove any adhering soft tissues. In one embodiment the connective tissue is reduced to a particle size. In an alternate embodiment the connective tissue is not reduced to a particle size.

The connective tissue can be reduced to a particle size by means including, but not limited to, mincing, dicing, grinding and the like. In one embodiment particle diameter is less than about 5 mm, preferably less than about 4 mm, more preferably less than about 3 mm. Most preferably, the particle diameter is about 0.1 mm to about 3 mm.

The terms "incubate" or "incubating" mean to maintain (a chemical or biochemical system) under specific conditions in order to promote a particular reaction.

As used herein the term "autolysis" refers to the digestion of cellular components by endogenous hydrolases and proteinases released from lysosomes or associated with the cell and its pericellular matrix following cell death, causing self digestion of tissue. A person skilled in the art will appreciate that the rate of autolysis will vary with many factors including pH, temperature, concentration, tissue type, tissue particle size and time of incubation.

The term "buffer" refers to a compound, usually a salt, which, when dissolved in an aqueous medium serves to maintain the free hydrogen ion concentration of the solution within a certain pH range, when hydrogen ions are added or removed from the solution. A salt or solution is said to have a "buffering capacity" or to buffer the solution over such a range, when it provides this function. Generally a buffer will have adequate buffering capacity over a range that is within ±1 pH unit of its pK.

In one embodiment the salt is a monovalent salt. Preferably the monovalent salt is selected from any one or more of hydrogen, sodium, potassium, or ammonium. In an alternate embodiment the salt is not a monovalent salt. In another embodiment the salt is a divalent salt selected from any one or more of calcium, magnesium, copper, or zinc. Most preferably the salt is calcium or magnesium.

In one embodiment the pH is in the range of about 2.5 to about 8.5, preferably about 3.5 to about 8.0, more preferably about 4 to about 7 and most preferably about 4.5 to about 7.

The term "condition" refers to other factors which affect the rate, efficiency and amount of autolysis, such as, for example, temperature and time.

In one embodiment the temperature conditions for carrying out the step of autolysis is in the range of from about 20° C. to about 45° C., preferably about 25° C. to about 45° C., more preferably about 32° C. to about 45° C., more preferably about 32° C. to about 40° C. most preferably about 37° C.

In one embodiment, the autolysis takes up to 48 hours, preferably up to 36 hours, preferably up to 24, preferably up to 16 hours, more preferably 16-24 hours.

In a preferred embodiment, cartilage particles of size 1-3 mm are subject to autolysis in an aqueous medium at a pH of 4-5 and temperature of 32-45° C. for 16-24 hours.

Glycosaminoglycan (GAG) refers to the polysaccharide chains of proteoglycans, which are composed of repeating disaccharide units containing a derivative of an amino sugar (either glucosamine or galactosamine) glycosidically linked to glucuronic or iduronic acid. The most common derivatives being O-sulfated esters substituted in the 4 or 6 positions of the N-acetylated glucosamine or galactosamine rings.

Examples of GAGs include hyaluronic acid (hyaluronan) (which is non-sulfated), chondroitin sulfate, keratan sulfate and heparan sulfate.

The terms "protein", "polypeptide", or "peptide", when used herein are interchangeable and refer to amino acids in a polymeric form of any length.

GAG-peptides and polypeptides can be recovered from the autolysis medium with well known methods. For example, in one embodiment, the residual tissue particles are removed by filtration from the autolysis media and the mixture of GAG-peptide complexes and polypeptides recovered from the supernatant. In another embodiment, the residual tissue particles are not removed from the autolysis medium.

In one embodiment, the supernatant is neutralised by addition of an alkaline solution containing a cation.

In one embodiment the supernatant is freeze dried. In an alternate embodiment the supernatent is not freeze dried.

Alternatively the mixture of GAG-peptide and polypeptide is recovered from the autolysis medium or supernatant by precipitation with excess quantities of acetone, or aliphatic alcohols, such as, for example, ethanol or methanol. In another embodiment, the mixture of GAG-peptide and polypeptide is recovered from the autolysis medium or supernatant by the formation of water insoluble complexes with quaternary ammonium salts such as cetyl pyridinium, chloride. In another embodiment the mixture of GAG-peptide and polypeptide are recovered from the autolysis medium or supernatant by separation using size exclusion or ion-exchange or other forms of column chromatography or membrane filtration technology.

2. Separating and Recovering the Polypeptides of the Invention

Following recovery of the mixture of the GAG-peptide and polypeptide, the polypeptide and GAG-peptide can be separated by methods well known in the art.

Preferably, the mixture of the GAG-peptide and the polypeptide is subjected to an ion exchange technique. In one embodiment the mixture of the GAG-peptide and the polypeptide is subjected to ion exchange solid phase media. In one embodiment the solid phase media is DEAE sepharose. In a preferred embodiment, the solid phase media is pre-swollen DEAE-Sepharose-6B.

Recovery of the polypeptide refers to any well known separation technique. In one embodiment the polypeptide can be recovered by, for example, chromatography, ion exchange techniques, gel filtration (eg. diafiltration or ultrafiltration), gel electrophoresis (eg. one dimensional or two dimensional) or any other method of separating polypeptides according to their size and molecular weight, or combination thereof, and which is capable of recovering polypeptides having a molecular weight of less than 30,000 Da.

A combination of the same or similar separation techniques may be used and may be repeated. In this way, fractions of polypeptides of different molecular weight ranges may be obtained and individual polypeptides can also be recovered. It will be understood that separation of polypeptides according to size and molecular may be performed in any order.

Accordingly, in one example the recovered polypeptides are subjected to a separation technique to recover polypeptides having a molecular weight of greater than 1,000 Da. The recovered polypeptides having a molecular weight of greater than 1,000 Da are subjected to a separation technique to recover polypeptides having a molecular weight of less than 30,000 Da. Accordingly, in one example the polypeptides have a molecular weight of less than 30,000 Da and greater than 1,000 Da.

In another example, the recovered polypeptides are subjected to a separation technique to recover polypeptides having a molecular weight of greater than 1,000 Da and then subjected to a separation technique to recover polypeptides having a molecular weight of greater than 10,000 Da.

Accordingly, examples of the invention relate to the recover of polypeptides having a molecular weight of less than 30,000 Da, less than 30,000 Da and greater than about 1,000 Da, and less than 30,000 and greater than 10,000.

In a further embodiment, the present invention comprises separating the one or more recovered polypeptides to recover individual polypeptides. Separation can be performed according to any well known techniques such as for example chromatography, one dimensional gel electrophoresis, two dimensional electrophoresis or the like.

The inventors have further analysed and identified the individual polypeptides separated by the method of the present invention.

Polypeptides recovered by the method of the invention are connective tissue derived polypeptides. The inventors have found that the recovered polypeptides and mixtures thereof have enhanced and/or different pharmacological activities to the GAG-peptide/polypeptide mixtures.

Accordingly, the present invention provides a connective tissue derived polypeptide, obtainable by the method of the invention, having anti-arthritic or anti-inflammatory activity. In one embodiment, polypeptides of the invention and mixtures thereof reduce rear paw inflammation in rats with collagen induced arthritis. In another embodiment, polypeptides of the invention and mixtures thereof decrease tail inflammation in rats with collagen induced arthritis. In another embodiment, polypeptides decrease fore paw inflammation in rats with collagen induced arthritis. In yet another embodiment, polypeptides of the invention and mixtures thereof decrease weight loss in rats with collagen induced arthritis.

As used herein the term "derived" shall be taken to indicate that a specified integer may be obtained from a source, albeit not necessarily directly from that source.

In an alternate embodiment, the polypeptides of the present invention are connective tissue derived polypeptides obtainable by the methods of the present invention having a molecular weight in the range of less than about 30,000 Da and having anti-arthritic or anti-inflammatory.

In an alternate embodiment, the polypeptides of the present invention are connective tissue derived polypeptides obtainable by the methods of the present invention having a molecular weight in the range of about 1,000 Da and about 30,000 Da and having anti-arthritic or anti-inflammatory.

In an alternate embodiment, the polypeptides of the present invention are connective tissue derived polypeptides obtainable by the methods of the present invention having a molecular weight in the range of about 10,000 Da and about 30,000 Da and having anti-arthritic or anti-inflammatory.

In another embodiment, the polypeptides of the present invention are connective tissue derived polypeptides obtainable by the methods of the present invention, having a molecular weight in the range of about 25,000 Da and about 30,000 Da and having anti-arthritic or anti-inflammatory.

Mixtures of polypeptides which have a molecular weight in a desired range are clearly contemplated.

In another embodiment, individual polypeptides obtainable by the methods of the invention having anti-arthritic or anti-inflammatory are contemplated. In one example the connective tissue derived polypeptides of the present invention have a molecular weight of about 27,000 Da.

In a preferred example, the present invention provides a connective tissue derived polypeptide having a molecular weight of about 10,000 Da to about 30,000 Da, having anti-arthritic or anti-inflammatory and selected from the group consisting of:

(a) a connective tissue derived polypeptide having an isoelectric point (pI) of about 6 to about 6.5, and more preferably a pI value of about 6.3 as determined by isoelectric focussing.

(b) a connective tissue derived polypeptide having an isoelectric point (pI) of about 6.5 to about 7, and more preferably a pI value of about 6.8 as determined by isoelectric focussing (c) a connective tissue derived polypeptide having an isoelectric point (pI) of about 7.5 to about 8.5, and more preferably a pI value of about 7.8 as determined by isoelectric focussing (d) a connective tissue derived polypeptide having an isoelectric point (pI) of about 8 to about 8.5, and more preferably a pI value of about 8.2 as determined by isoelectric focussing (e) a connective tissue derived polypeptide having an isoelectric point (pI) of about 8 to about 8.5, and more preferably a pI value of about 8.3 as determined by isoelectric focussing (f) a connective tissue derived polypeptide having an isoelectric point (pI) of about 8.3 to about 8.8, and more preferably a pI value of about 8.6 as determined by isoelectric focussing (g) a connective tissue derived polypeptide having an isoelectric point (pI) of about 8.8 to about 9.5, and more preferably a pI value of about 9.1 as determined by isoelectric focussing (h) a connective tissue derived polypeptide having an isoelectric point (pI) of about 6 to about 6.5, and more preferably a pI value of about 6.2 as determined by isoelectric focussing (i) a connective tissue derived polypeptide having an isoelectric point (pI) of about 6.8 to about 7.5, and more preferably a pI value of about 7.2 as determined by isoelectric focussing Individual polypeptides of the invention have been identified as fragments of known proteins. Peptides of up to about 30 amino acids were produced by subjecting a polypeptide to trypsin digestion and then to Matrix Assisted Laser Desorption Ionisation (MALDI) mass spectrometry. The peptides have been compared to known proteins provided in reference databases.

Accordingly, in another embodiment, the present invention provides an isolated polypeptide obtainable by the method of the invention comprising the sequences and % match with known proteins as disclosed in FIG. 4, wherein the polypeptide or polypeptide fragment has anti-arthritic or anti-inflammatory.

Preferably, the connective tissue derived polypeptide in paragraph (a) supra comprises one or more of the following sequences following trypsin digestion:

| | |
|---|---|
| (K)LGNNV DFR(I) | (SEQ ID NO. 4) |
| (R)IESLP IKPR(G) | (SEQ ID NO. 5) |
| (R)HLYPN GLPEE YSFLT TFR(M) | (SEQ ID NO. 8) |
| (K)IMIGV ER(S) | (SEQ ID NO. 3) |
| (R)SSATL FVDCN R(I) | (SEQ ID NO. 11) |

Preferably, the connective tissue derived polypeptide in paragraph (b) supra comprises one or more of the following sequences following trypsin digestion:

| | |
|---|---|
| (K)SVSFS YK(G) | (SEQ ID NO. 2) |
| (K)IMIGV ER(S) | (SEQ ID NO. 3) |
| (K)LGNNV DFR(I) | (SEQ ID NO. 4) |
| (R)IESLP IKPR(G) | (SEQ ID NO. 5) |
| (K)HWSIW QIQDS SGK(E) | (SEQ ID NO. 6) |
| (R)IGQDD LPGFD LISQF QIDK(A) | (SEQ ID NO. 7) |
| (R)HLYPN GLPEE YSFLT TFR(M) | (SEQ ID NO. 8) |
| (K)GLDGS LQTAA FSNLP SLFDS QWHK(I) | (SEQ ID NO. 9) |
| (K)IMIGV ER(S) | (SEQ ID NO. 10) |
| (R)SSATL FVDCN R(I) | (SEQ ID NO. 11) |

Preferably, the connective tissue derived polypeptide in paragraph (c) supra comprises one or more of the following sequences following trypsin digestion:

| | |
|---|---|
| (K)SVSFS YK(G) | (SEQ ID NO. 2) |
| (K)IMIGV ER(S) | (SEQ ID NO. 3) |
| (K)LGNNV DFR(I) | (SEQ ID NO. 4) |
| (R)IESLP IKPR(G) | (SEQ ID NO. 5) |
| (K)HWSIW QIQDS SGK(E) | (SEQ ID NO. 6) |
| (R)IGQDD LPGFD LISQF QIDK(A) | (SEQ ID NO. 7) |
| (R)HLYPN GLPEE YSFLT TFR(M) | (SEQ ID NO. 8) |
| (K)GLDGS LQTAA FSNLP SLFDS QWHK(I) | (SEQ ID NO. 9) |
| (K)IMIGV ER(S) | (SEQ ID NO. 10) |
| (R)SSATL FVDCN R(I) | (SEQ ID NO. 11) |

Preferably, the connective tissue derived polypeptide in paragraph (d) supra comprises one or more of the following sequences following trypsin digestion:

| | |
|---|---|
| (K)SVSFS YK(G) | (SEQ ID NO. 2) |
| (K)IMIGV ER(S) | (SEQ ID NO. 3) |
| (K)LGNNV DFR(I) | (SEQ ID NO. 4) |
| (R)IESLP IKPR(G) | (SEQ ID NO. 5) |
| (K)HWSIW QIQDS SGK(E) | (SEQ ID NO. 6) |
| (R)HLYPN GLPEE YSFLT TFR(M) | (SEQ ID NO. 8) |
| (K)GLDGS LQTAA FSNLP SLFDS QWHK(I) | (SEQ ID NO. 9) |
| (R)SSATL FVDCN R(I) | (SEQ ID NO. 11) |

Preferably, the connective tissue derived polypeptide in paragraph (e) supra comprises one or more of the following sequences following trypsin digestion:

| | |
|---|---|
| (K)LGNNVDFR(I) | (SEQ ID NO. 4) |
| (R)IESLPIKPR(G) | (SEQ ID NO. 5) |

| | |
|---|---|
| (R)IGQDD LPGFD LISQF QIDK(A) | (SEQ ID NO. 7) |
| (R)HLYPN GLPEE YSFLT TFR(M) | (SEQ ID NO. 8) |
| (R)SSATL FVDCN R(I) | (SEQ ID NO. 11) |

Preferably, the connective tissue derived polypeptide in paragraph (f) supra comprises one or more of the following sequences following trypsin digestion:

| | |
|---|---|
| (K)SVSFS YK(G) | (SEQ ID NO. 2) |
| (K)IMIGV ER(S) | (SEQ ID NO. 3) |
| (K)LGNNV DFR(I) | (SEQ ID NO. 4) |
| (R)IESLP IKPR(G) | (SEQ ID NO. 5) |
| (K)HWSIW QIQDS SGK(E) | (SEQ ID NO. 6) |
| (R)IGQDD LPGFD LISQF QIDK(A) | (SEQ ID NO. 7) |
| (R)HLYPN GLPEE YSFLT TFR(M) | (SEQ ID NO. 8) |
| (K)IMIGV ER(S) | (SEQ ID NO. 10) |
| (R)SSATL FVDCN R(I) | (SEQ ID NO. 11) |

Preferably, the connective tissue derived polypeptide in paragraph (g) supra comprises one or more of the following sequences following trypsin digestion:

| | |
|---|---|
| (K)LGNNV DFR(I) | (SEQ ID NO. 4) |
| (R)IESLP IKPR(G) | (SEQ ID NO. 5) |
| (R)IGQDD LPGFD LISQF QIDK(A) | (SEQ ID NO. 7) |
| (R)HLYPN GLPEE YSFLT TFR(M) | (SEQ ID NO. 8) |
| (R)SSATL FVDCN R(I) | (SEQ ID NO. 11) |

Preferably, the connective tissue derived polypeptide in paragraph (h) supra comprises one or more of the following sequences following trypsin digestion:

| | |
|---|---|
| (K)SVSFS YK(G) | (SEQ ID NO. 2) |
| (K)IMIGV ER(S) | (SEQ ID NO. 3) |
| (K)LGNNV DFR(I) | (SEQ ID NO. 4) |
| (R)IESLP IKPR(G) | (SEQ ID NO. 5) |
| (K)HWSIW QIQDS SGK(E) | (SEQ ID NO. 6) |
| (R)IGQDD LPGFD LISQF QIDK(A) | (SEQ ID NO. 7) |
| (R)HLYPN GLPEE YSFLT TFR(M) | (SEQ ID NO. 8) |
| (K)IMIGV ER(S) | (SEQ ID NO. 10) |
| (R)SSATL FVDCN R(I) | (SEQ ID NO. 11) |

Preferably, the connective tissue derived polypeptide in paragraph (i) supra comprises one or more of the following sequences following trypsin digestion:

| | |
|---|---|
| (K)SVSFS YK(G) | (SEQ ID NO. 2) |
| (K)IMIGV ER(S) | (SEQ ID NO. 3) |
| (K)LGNNV DFR(I) | (SEQ ID NO. 4) |

-continued

| | | |
|---|---|---|
| (R)IESLP IKPR(G) | | (SEQ ID NO. 5) |
| (K)HWSIW QIQDS SGK(E) | | (SEQ ID NO. 6) |
| (R)IGQDD LPGFD LISQF QIDK(A) | | (SEQ ID NO. 7) |
| (R)HLYPN GLPEE YSFLT TFR(M) | | (SEQ ID NO. 8) |
| (K)IMIGV ER(S) | | (SEQ ID NO. 3) |
| (R)SSATL FVDCN R(I). | | (SEQ ID NO. 11) |

Preferably, the connective tissue derived polypeptide in paragraphs (a)-(i) supra comprises an amino acid sequence having substantial identity to the sequence of Type IX collagen alpha 1 chain NC4 domain as depicted in Table 1 below or a homologue or derivative thereof

TABLE 1

Physical Characteristics of Protein fragments found in Calcium Peptacan after ion-exchange treatment and 2D electrophoresis.

| Fragment ID# | Estimated isoelectric point | Estimated Molecular Weight |
|---|---|---|
| 1 | 4.0 | 74 kDa |
| 2 | 4.1 | 65 kDa |
| 3 | 3.9 | 50 kDa |
| | (this band has now been shown to correspond to fragments from 2 or 3 proteins identified as bovine COMP and either bovine alpha-1 antiprotease inhibitor or Endopin-1) | |
| 4 | 3.7 | 45 kDa |
| 5 | 3.4 | 40 kDa |
| 6 | 4.6 | 50 kDa |
| 7 | 6.3 | 67 kDa |
| 8 | 6.1 | 65 kDa |
| 9 | 6.3 | 60 kDa |
| 10 | 6.3 | 38 kDa |
| 11 | 6.0 | 30 kDa |
| 12 | 6.4 | 25 kDa |
| 13 | 6.8 | 22 kDa |
| 14 | 7.8 | 20 kDa |
| 15 | 8.2 | 18 kDa |
| 16 | 8.3 | 19 kDa |
| 17 | 8.6 | 20 kDa |
| 18 | 9.1 | 19 kDa |
| 19 | 5.3 | 12 kDa |
| 20 | 6.2 | 22 kDa |
| 21 | 7.2 | 21 kDa |

Table 1 shows the physical characteristics (MW and pI) of protein fragments polypeptides found in Calcium Peptacan after ion-exchange treatment and 2D electrophoresis as described in FIG. 4.

3. Polypeptides

The present inventors have substantially purified and established the identity of the type IX collagen alpha 1 chain polypeptide which is produced during the autolytic processing of bovine cartilage matrix.

Also incorporated herein are amino sequences for collagen type IX alpha 1 NC4 domain derived from human, chick and rat connective tissue. Amino acid sequence comparisons of the bovine-chick NC4 domain polypeptides (see Table 2 below), and bovine-human NC4 domain polypeptides (see Table 3 below) show sequence overlap.

Table 2 below shows the amino acid sequence of the NC4 domain of the type IX collagen alpha 1 chain from 17 day old chick embryos sterna as reported by Vasios et al. (J Biological Chem. 263, 2324-2329, 1998) on which the amino acid sequences identified from the MALDI-MS analysis of the polypeptides separated by 2D electrophoresis have been superimposed indicating where the sequences are identical as bold type and underlined.

TABLE 2

(SEQ ID NO. 1)
PRO-ARG-PHE-PRO-VAL-ASN-SER-ASN-SER-ASN/GLY-GLU-

ASN-GLU-LEU-CYS-PRO-LYS-VAL-ARG/ILE-GLY-GLN-ASP-

ASP-LEU-PRO-GLY-PHE-ASP/LEU-ILE-SER-GLN-PHE-GLN-

ILE-ASP-LYS-ALA/ALA-SER-ARG-ARG-ALA-ILE-GLN-ARG-

VAL-VAL/GLY-SER-THR-ALA-LEU-GLN-VAL-ALA-TRY-LYS/

LEU-GLY-ASN-ASN-VAL-ASP-PHE-ARG/THR-ARG-HIS-LEU-

TYR-PRO-ASN-GLY-LEU-PRO/GLU-GLU-TYR-SER-PHE-LEU-

THR-THR-PHE-ARG/MET-THR-GLY-SER-THR-LEU-GLY-LYS-

HIS-TRP/SER-ILE-TRP-GLN-ILE-GLN-ASP-SER-SER-GLY/

LYS-GLU-GLN-VAL-GLY-VAL-LYS-ILE-ASN-GLY/GLN-THR-

LYS-SER-VAL-SER-PHE-SER-TRY-LYS/GLY-LEU-ASP-GLY-

SER-LEU-GLN-THR-ALA-ALA/PHE-SER-ASN-LEU-PRO-SER-

LEU-PHE-ASP-SER/GLN-TRP-HIS-LYS-ILE-MET-ILE-GLY-

VAL-GLU/ARG-SER-SER-ALA-THR-LEU-PHE-VAL-ASP-CYS/

ASN-ARG-ILE-GLU-SER-LEU-PRO-ILE-LYS-PRO

Table 3 below shows the human NC4 domain of the type IX collagen alpha 1 chain (sequences 24-268) obtained from the Swiss-Prot & TrEMBL data-bases (released 7 Jun. 2004) on which the amino acid sequences identified from the MALDI-MS analysis of the polypeptides separated by 2D electrophoresis have been superimposed showing where the sequences are identical as bold type and underlined. Sequence 1-23 is the signal sequence for the human NC4 domain of the type IX collagen alpha 1 chain.

TABLE 3

(SEQ ID NO. 15)
1 Met Lys Thr Cys Trp Lys Ile Pro Val Phe Phe Val Cys Ser 16 Phe Leu Glu Pro

Trp Ala Ser Ala 23 Ala Val Lys Arg Arg Pro Arg 31 Phe Pro Val Asn Ser Asn Ser

Asn Gly Gly Asn Glu Leu Cys Pro 46 Lys Ile Arg Ile Gly Gln Asp Asp Leu Pro Gly

Phe Asp Leu Ile 61 Ser Gln Phe Gln Val Asp Lys Ala Ala Ser Arg Arg Ala Ile Gln

TABLE 3-continued

```
76 Arg Val Val Gly Ser Ala Thr Leu Gln Val Ala Tyr Lys Leu Gly 91 Asn Asn Val

Asp Phe Arg Ile Pro Thr Arg Asn Leu Tyr Pro Ser 106 Gly Leu Pro Glu Glu Tyr Ser

Phe Leu Thr Thr Phe Arg Met Thr 121 Gly Ser Thr Leu Lys Lys Asn Trp Asn Ile

Trp Gln Ile Gln Asp 136 Ser Ser Gly Lys Glu Gln Val Gly Ile Lys Ile Asn Gly Gln

Thr 151 Gln Ser Val Val Phe Ser Tyr Lys Gly Leu Asp Gly Ser Leu Gln 166 Thr

Ala Ala Phe Ser Asn Leu Ser Ser Leu Phe Asp Ser Gln Trp 181 His Lys Ile Met Ile

Gly Val Glu Arg Ser Ser Ala Thr Leu Phe 196 Val Asp Cys Asn Arg Ile Glu Ser

Leu Pro Ile Lys Pro Arg Gly 211 Pro Ile Asp Ile Asp Gly Phe Ala Val Leu Gly Lys

Leu Ala Asp 226 Asn Pro Gln Val Ser Val Pro Phe Glu Leu Gln Trp Met Leu Ile 241

His Cys Asp Pro Leu Arg Pro Arg Arg Glu Thr Cys His Glu Leu 256 Pro Ala Arg Ile

Thr Pro Ser Gln Thr Thr Asp Glu Arg 268
```

By "substantially purified polypeptide" we mean a polypeptide that has been at least partially separated from the lipids, nucleic acids, other polypeptides, and other contaminating molecules with which it is associated in its native state. Preferably, the substantially purified polypeptide is at least 60% free, preferably at least 75% free, and most preferably at least 90% free from other components with which they are naturally associated. Furthermore, the term "polypeptide" is used interchangeably herein with the term "protein".

The % identity of a polypeptide is determined by GAP (Needleman and Wunsch, 1970) analysis (GCG program) with a gap creation penalty=5, and a gap extension penalty=0.3. Unless stated otherwise, the query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. Even more preferably, the query sequence is at least 100 amino acids in length and the GAP analysis aligns the two sequences over a region of at least 100 amino acids.

With regard to the defined polypeptides/enzymes, it will be appreciated that % identity figures higher than those provided above will encompass preferred embodiments. Thus, where applicable, in light of the minimum % identity figures, it is preferred that the polypeptide comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

As used herein, the term "biologically active fragment" refers to a portion of the defined polypeptide which still maintains anti-arthritic or anti-inflammatory activity (whichever is relevant). Such biologically active fragments can readily be determined by serial deletions of the full length protein, and testing the activity of the resulting fragment.

Amino acid sequence mutants/variants of the polypeptides/enzymes defined herein can be prepared by introducing appropriate nucleotide changes into a nucleic acid encoding the polypeptide, or by in vitro synthesis of the desired polypeptide. Such mutants include, for example, deletions, insertions or substitutions of residues within the amino acid sequence. A combination of deletion, insertion and substitution can be made to arrive at the final construct, provided that the final protein product possesses the desired characteristics.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 30 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active or binding site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 4.

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn, his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides of the present invention can be produced in a variety of ways, including production and recovery of natural proteins, production and recovery of recombinant proteins, and chemical synthesis of the proteins. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

4. Preparation and Administration of Pharmaceutical Compositions

Compositions of the invention may be prepared from one or more polypeptide. Additional polypeptide fragments or peptides can be identified by routine experimentation in light of the present specification and figures. A method for identifying peptide fragments having stimulatory activity is described, for example, in U.S. Pat. No. 5,399,342.

The pharmaceutical compositions may be for human or animal usage in human and veterinary medicine and will typically comprise any one or more of a pharmaceutically acceptable diluent, carrier or excipient. Acceptable carriers or diluents for therapeutic use are well known in the pharmaceutical art, and are described for example in *Remington's Pharmaceutical Sciences* Mack Publishing Co. (A. R. Gennaro edit. 1985). The choice of pharmaceutical carrier excipient or diluent can be selected with regard to the intended route of administration and standard pharmaceutical practice. The pharmaceutical compositions may comprise as, or in addition to, the carrier, excipient or diluent, any suitable binder, lubricant, suspending agent, coating agent, or solubilizing agent.

It is well known in the art that there may be different composition/formulation requirements dependant on the different delivery systems.

According to the present invention non-invasive formulations are particularly preferred. Where appropriate, the pharmaceutical compositions can be administered by inhalation, orally or intranasally, in the form of suppository or pessary, topically in the form of a lotion, solution, cream, ointment, or dusting powder, by use of a skin patch, orally in the form of tablets containing excipients such as starch or lactose, or in capsules, chewables or ovules either alone or in admixture with excipients, or in the form of elixirs, solutions, syrups or suspensions containing flavouring or colouring agents.

For buccal or sublingual administrations, the compositions may be administered for example in the form of tablets or lozenges which can be formulated in a conventional manner.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Intranasal formulations are described and administration of larthrytic collagen type II and larthrytic collagen type IX are described for example in Lu et al (1999) Different therapeutic and bystander effects by intranasal administration of homologous type II and type IX collagens on the collagen-induced arthritis and pristane-induced arthritis in rats, *Clinical Immunology* Vol 90 pp 119-127 (1999).

In another example, the pharmaceutical composition of the present invention may be formulated to be delivered using a mini-pump or by a mucosal route, for example, as a nasal spray or aerosol for inhalation or ingestible solution.

Where the agent is to be delivered mucosally through the gastro-intestinal mucosa, it should be able to remain stable during transit through the gastro-intestinal tract; for example, it should be resistant to proteolytic degradation, stable antacid, pH and resistant to the detergent effects of bile.

Preferably, the compositions of the invention are administered by a non-invasive route. Preferably, the non-invasive route comprises oral administration, or enteral administration, nasal administration or by inhilation.

In an alternate embodiment, compositions of the invention can be injected parenterally for example, intravenously, intramuscularly or subcutaneously.

For parenteral administration, the compositions may be best used in the form of a sterile aqueous solution which may contain other substances, for example enough salts or monosaccharides to make the solution isotonic with blood. The preparation may also be emulsified, or encapsulated in liposomes.

After formulation, the immuno-protective composition may be incorporated into a sterile container which is then sealed and stored at a low temperature, for example 4° C., or it may be freeze-dried. Lyophilisation permits long-term storage in a stabilised form.

5. Treatment and Protection of an Individual

The effects observed for the polypeptides on inflammation and collagen induced arthritis in rats also provide application for the polypeptides, and mixtures thereof, in the treatment, and protection of an individual to arthritis and other degenerative diseases. Further the effects observed provide application of the polypeptides in the tolerisation of an individual to the antigenic effects of cartilage components. Further, the finding provide application to methods of restoration of connective tissues, particularly in inflammatory and degenerative tissue diseases such as rheumatoid arthritis and osteoarthritis.

Polypeptides according to the invention that have been shown to have anti-inflammatory and/or anti-arthritic activity can be further tested for safety and efficacy in other animal models, and then proceed to clinical trials in humans, if desired. Naturally, for veterinary applications, no clinical trial in humans is required. Those polypeptides that are safe and efficacious in animals or humans can be administered to an appropriate subject to treat a connective tissue disease, or alternatively to protect against connective tissue disease by the process of tolerisation.

Rodent models of connective tissue disease are well known. For example, rat models for collagen induced arthritis and pristane induced arthritis rats are described in Lu et al (1999) (supra). Murine collagen induced models of arthritis are also described in Myers et al (2002) (supra).

Methods and pharmaceutical formulations for the treatment of autoimmune arthritis and animal models in mammals, including humans, by the oral, enteral or by—inhalation administration of whole collagen type II protein or biologically active peptide fragments of collagen type II are described in U.S. Pat. No. 5,399,347 (Trentham et al). Further, methods and formulations for evaluating the efficacy of oral type II collagen in the treatment of juvenile rheumatoid arthritis (JRA) are described in Barnett et al (1996) (supra).

Intranasal formulations are described and administration of larthrytic collagen type II and larthrytic collagen type IX are described in Lu et al (1999) (supra).

The present invention provides methods of treatment of arthritis or other degenerative disease in animals, preferably mammals and more preferably humans.

"Treatment and protection" includes both prophylactic and therapeutic measures to prevent the onset and appearance of a connective tissue disease as well as to prevent the onset and appearance of an abnormal immune response against the body's own tissues involved in autoimmune disease. The term also encompasses the suppression or mitigation of the abnormal (cell and/or humoral) immune response to the body's own collagen or more generally cartilage as well as the alleviation or elimination of clinical symptoms after the onset (ie. clinical manifestation) of autoimmune disease.

"Autoimmune disease" is defined as a malfunction of the immune system of mammals, in which the immune system fails to distinguish between foreign substances within the mammal and/or autologous tissues or substances and, as a result, treats autologous tissues and substances as if they were foreign and mounts an immune response against them.

Tolerance

The present invention provides methods for inducing tolerance in an individual to at least one antigenic component of cartilage.

As used herein "tolerance" refers to the active state of specific immunologic nonresponsiveness induced by prior exposure to an antigen. Experimentally induced tolerance may be defined as a state in which an animal will fail to respond to an antigen that will normally be immunogenic. Immunologic tolerance does not simply reflect the absence of an immune response, but rather an active response of the immune system that exhibits antigenic specificity and memory—the hallmarks of any immune response. In experimentally induced tolerance a foreign antigen is administered under certain conditions that promotes a state of tolerance rather than immune activation. Antigen structure, dosage and route of administration each partly determine whether the response of the immune system will lead to immunity or tolerance. Experimental evidence demonstrating the role of these factors is provided in J. Kuby in *Immunology*, 2nd ed, WH Freeman and Company, 1994, Chapter 16.

As used herein the terms "immunotherapy" and "tolerance therapy" refer to any general method resulting in tolerance or immunological prophylaxis. In vivo, these therapies typically entail a series of parenteral or oral administrations of the immunogenic material over an extended period of time. In one embodiment, "tolerance therapy" refers to a method for the down-regulation of an immune response, eg., to suppress an inflammatory response to an auto-antigen.

Oral administration of antigens is an effective method of inducing peripheral T-cell tolerance. This phenomenon, often referred to as oral tolerance, has been well studied in various models of autoimmune diseases in animals including encephalomyelitis, uveitis, diabetes, myasthenia gravis, and arthritis. The mechanisms for inducing tolerance, however, are not completely understood. All of the known mechanisms for tolerance induction, including clonal anergy, clonal deletion, and regulation by IL-4, IL-10, or TGF-beta-mediated active suppression may have a role in oral tolerance. Generally, higher doses of antigen are reported to induce anergy or clonal deletion whereas low doses induce cytokine regulation and active suppression.

Active suppression describes the regulation of one lymphocyte subset by another in an antigen-specific manner. Depending on the antigen and disease state, the suppressor cells may be CD4+ and/or CD8+ T-lymphocytes which migrate from peripheral lymphoid tissues, such as spleen and peripheral lymph nodes, to sites of disease activity. Adoptive transfer of these cells to naive recipients has confirmed the role of these cells in active suppression in rodent models of ovalbumin-induced hypersensitivity, and multiple sclerosis. In vitro evidence of active suppression is demonstrated by data showing that tolerized lymphocytes from animals can suppress proliferation of other antigen-specific T-lymphocytes across a transwell cell culture system (Faria and Weiner, "Oral tolerance: mechanisms and therapeutic applications," Adv. Immunol., 73:153-264, 1999).

Clonal anergy refers to unresponsiveness of antigen-specific T-lymphocytes, which is characterized by diminished proliferation after exposure to an antigen, and is involved in oral tolerance in several animal models. Anergy could be the result of production of soluble suppressive factors by CD4+ or CD8+ T-lymphocytes themselves, other T-lymphocytes or cells in the local environment, or as result of decreased expression of appropriate costimulatory molecules. Clonal deletion refers to the elimination of antigen-specific T-lymphocytes, but has been reported rarely as a mechanism of oral tolerance to an antigen (Chen, Inobe, Marks, Gonnella, Kuchroo, Weiner, "Peripheral deletion of antigen-reactive T cells in oral tolerance," Nature, 376:177-180, 1995).

The soluble mediators that suppress the immune response during oral tolerance are derived mainly from regulatory or suppressor T-lymphocytes (Faria and Weiner 1999, supra). There are four types of T-lymphocytes described by the cytokines they produce: Th1-type that produce interleukin-2 (IL-2) and gamma interferon (K FN); Th2-type that produce IL-4 and IL-10; Th3-type that produce high levels or transforming growth factor beta (TGF-θ), alone, or in conjunction with very low levels of IL-4, IL-10, or K.IFN; and Tr1 cells that produce high levels of IL-10 in conjunction with low levels of TGF-θ. Since Th3, Th2, and Tr1-T-lymphocytes have been shown to be the major mediators of active suppression induced by oral tolerance, then TGF-θ, IL-4 and IL-10 are believed to be key cytokines in this process Further reports showing that oral tolerance induction occurred in the absence of these cytokines suggests that other mediators or cells could suppress the immune response.

Studies of tolerance have focused primarily on the effect of the tolerizing antigen on T-lymphocyte function, and the role of T-lymphocytes in suppressing immune activation. However, immune responses to any antigen require interactions between APC's and T-lymphocytes, and the T-lymphocyte may affect APC function. Therefore, down-regulated antigen presentation by APC's from tolerized hosts could also contribute to tolerance induction either indirectly as a result of interactions with suppressor T-lymphocytes, or possibly as a result of direct effects of the tolerizing antigen on the APC.

As used herein "degenerative disease", "degenerative condition" or "degenerative disorder" are used interchangeably to refer to conditions that are characterised by a breakdown of a biological tissue, more particularly a connective tissue. Connective tissue refers to those animal tissue that supports organs, fills spaces between them, or performs mechanical functions such as connecting muscles to bone (tendons and ligaments) or providing low friction weighing surface as in articular cartilage. Connective tissues are characterized by their relatively avascular matrices and low cell densities. The most abundant connective tissues are the reticular stroma, muscle, adipose tissue, cartilage and bone.

The term "tissue" as used herein refers to matrices which contain similarly specialised cells that perform a common function. As used herein, tissue is intended to include an organ composed of a given tissue, and to the cells individually or collectively that compose the tissue.

As used herein "autoimmune disease" refers to a disease characterised by a humoral (eg., antibody-mediated), cellular (eg., cytotoxic T-lymphocyte-mediated), or a combination of both types of immune responses to epitopes on self-antigens. The immune system of the affected individual activates inflammatory cascades aimed at cells and tissues presenting those specific-self antigens. The destruction of the antigen, tissue, cell type or organ attacked gives rise to further symptoms of the disease. In a preferred embodiment of the invention the disease is selected from the group consisting of rheumatoid arthritis, osteoarthritis, disc degeneration and osteoporosis.

The terms self-antigens or auto-antigens are used interchangeably to refer to an antigen that is endogenous to an individual's physiology, that is recognised by either the cellular component (eg T-cell or B-cell receptors) or humeral component (antibodies) of that individual's system.

MODES FOR CARRYING OUT THE INVENTION

1. Experimental Protocols

Bovine, ovine, cervine or porcine tracheal cartilage or nasal cartilage, chicken sternal cartilage, or skeletal shark cartilage or deer antler cartilage were freed of adhering soft tissues mechanically or as described previously U.S. Pat. No. 5,399,347 March 1995, U.S. Pat. No. 5,364,845 December 1996, U.S. Pat. No. 6,025,327 February 2000). These cleaned hyaline cartilages were rinsed with water, minced into 1 mm or 3 mm sizes, freeze dried and stored at −20° C. Bovine tracheal chondroitin sulfate A (ChSA) was purchased from Sigma Chemical Co, USA or was obtained as a gift from Bioiberica, Barcelona, Spain (batch 1/0015, batch 05/2001, batch 18/11/99). All other chemicals were of analytical grade and were purchased from local suppliers.

Release of Glycosaminoglycan Peptide (GAG-Peptide) Complexes and Polypeptides from the Cartilage Powders Studies on the kinetics of release of the GAG-peptides and polypeptides from the cartilage powders were performed using different buffers (eg sodium or calcium acetate or dilute acetic acid) to give various products referred to herein as "Peptacan(s)" and was undertaken under a variety of conditions. The objective of these experiments was to determine the effects of (i) particle size—3 mm, 5 mm, (ii) different pHs eg. pH range 3.5-7.0, (iii) different temperatures, 4° C., 25° C. and 37° C., and (iv) animal species and tissue locations on the rate of autolysis and product release into the aqueous phase. All the experiments were performed, with stirring and release of sulphated GAGs and polypeptides monitored over 24 hours. In the initial studies undertaken, the primary observation was that subjecting particles of cartilages to autolysis in aqueous buffers maintained within the pH range of 4.0-7.0, particularly 4.5, preferably at 37° C. for periods up to 24 hours specifically released more than 80% of the total sulfated glycosaminoglycans (S-GAG) into solution. Studies also showed that the rate of release was dependent on the cartilage particle size, the smaller preparations undergoing more rapid release. However, by 24 hours the yields obtained were the same. The pH and temperature were found to be important determinants of the rate of release which indicated that the release process was mediated by endogenous enzymes present within the solid tissues. This proposed mechanism was confirmed by undertaking autolysis experiments in the absence and presence of specific enzyme inhibitors. Since it was found that the addition of N-ethylmaleimide produced the most significant inhibition of GAG-peptide and polypeptides release into the aqueous medium we consider that the cysteine class of proteinases, such as the Cathepsins, were the major, but not exclusive, contributors to the autolytic process.

The aqueous phase was separated from the cartilage powders by filtration and the filtrate centrifuged to remove fine particles and then neutralised to pH 7.0 by addition of an alkaline solution containing the desired cation. These Peptacan solutions after chemical analysis were either freeze dried and used directly for pharmacological studies. The freeze dried Peptacans were used as stock material for the preparation of dialysed and fractionated preparations as described below.

Alternatively the Peptacans could be isolated from the aqueous solutions obtained from the cartilage digests by precipitation with excess quantities of acetone, ethanol or methanol, usually by adding 3-5× the volume of the aqueous extracts. The precipitates so obtained would be washed with absolute ethanol and dried under vacuum then stored in a vacuum desiccator.

The process of the present invention is essentially non-disruptive leaving the type II collagen matrix and cells of the tissue intact, and the absence of DNA in the autolysis media. The efficiency of the autolytic process was also influenced by the animal species and anatomical location from where the cartilage was derived as well as the nature of the buffers used.

For the further experiments described herein, the results were obtained following subjecting bovine tracheal cartilage to autolysis with calcium acetate buffer. For the purpose of convenience, the product obtained by this process is referred to herein as Calcium Peptacan (CaP).

Separation of Glycosaminoglycan Peptides (GAG-Peptides) from Polypeptides in Peptacan Preparations by Ion-Exchange Solid Phase Media (See Schema Shown in FIG. 2)

Freeze-dried Peptacans was dissolved in 0.1M calcium chloride buffered with Tris-HCl to a pH of 7.2 (application buffer) to afford sample concentrations of 4.0 mg/ml. To these solutions was added pre-swollen DEAE-Sepharose-6B to achieve a final concentration of the ion exchanger of 100 mg/mL. This mixture was maintained at room temperature with gentle agitation for 16 hours in 5 mL stoppered centrifuge tubes. The tubes were then centrifuged at 1000 rpm for 5 mins and the supernatant decanted off. To the remaining pellet was added 1 mL of the application buffer and the tubes gently shaken, centrifuged again and the application buffer washings added to the original supernatant. The supernatant and washings contains the proteins and polypeptides in the Peptacan preparations.

Fractionation of the Peptacan Proteins and Polypeptides

Figure 3:
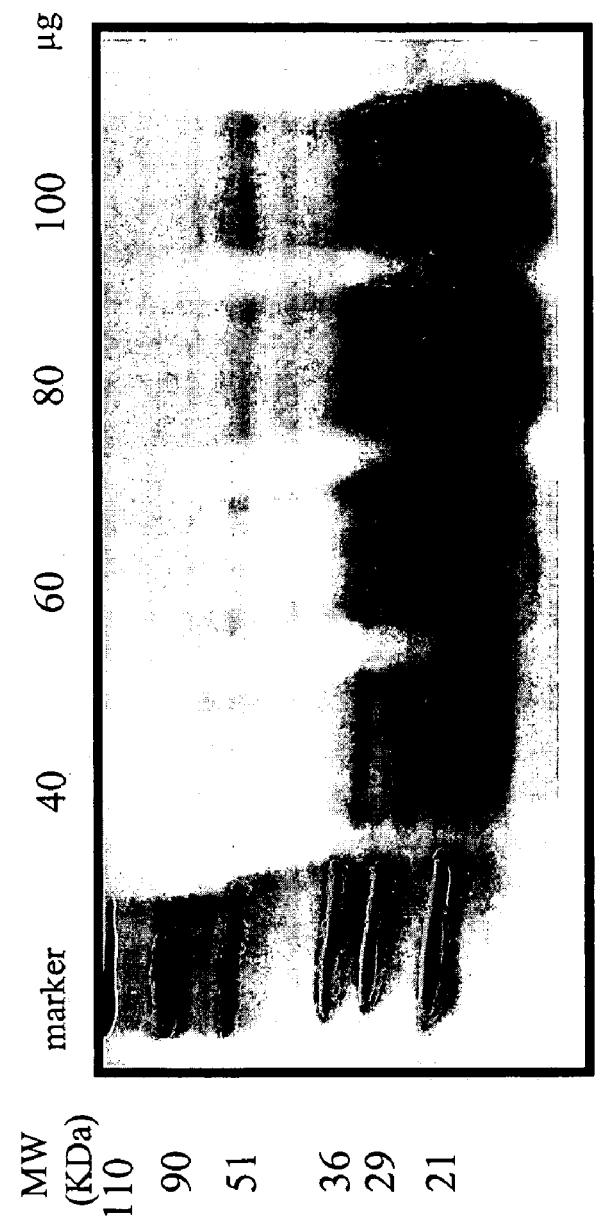
FIG. 3 is a photographic representation of the SDS-PAGE 1-D electrophoresis of the proteins/polypeptides isolated from the glycosaminoglycan-peptide and polypeptide mixture (CaP) using the ion-exchange schema shown in FIG. 2.

The supernatant and washings from the ion exchange process were subjected to diafiltration using a 1000 Da cut-off ultrafiltration membrane (eg, YC10) or a tangental flow ultrafiltration (TFF) cartridge of similar cut-off (Millipore Australia Pty Ltd, Sydney, Australia), to remove the inorganic ions. The diafiltrated de-salted polypeptide solution was then freeze-dried and stored at −20° C. Subjecting aqueous solutions of these polypeptides to further fractionation using TFF membranes of different molecular weight cut-offs afforded polypeptides of predetermined molecular size. For example using a PLTC regenerated cellulose membrane with an exclusion size of 30,000 (Millipore Australia Pty Ltd, Sydney, Australia) afforded a mixture of polypeptides in the retentate with molecular weights greater than 30,000 Da. These proteins and polypeptides were freeze dried and assigned the code of INR-307 for subsequent experiments. The dialysate from the first TFF contained polypeptides with molecular weights less than 30,000 Da but greater than 1,000 Da. This fraction was designated the code INR-126 for subsequent experiments. In addition the dialysate from the 30,000 Da TFF step was also subject to TFF using a polyethersulfone spiral cartridge (Millipore Australia Pty Ltd, Sydney, Australia) with an exclusion size of 10,000 Da which provided a retentate containing polypeptides with molecular weights >10,000 Da. These polypeptides were assigned the code INR-195 for subsequent experiments. The efficiency of the separations of these polypeptides into the molecular ranges cited was confirmed by SDS-PAGE using proteins of known molecular weight as standards such as those shown in FIGS. 3 and 4.

Further fractionation of the polypeptide solutions can be achieved using any one or combination of techniques such as, for example, gel filtration, ultrafiltration, SDS PAGE electrophoresis, 2D gel electrophoresis, and reverse phase HPLC using established methods (see for example, Eyre D, et al. Collagen type IX: evidence for covalent linkages to type II collagen in cartilage. FEB 220:337-341, 1987).

Detailed Preparation of INR-195

In this procedure the supernatant and washings containing the polypeptide components obtained from ion exchange separation of calcium peptacan using DEAE-Sepharose were transferred to a reservoir connected via a peristaltic pump to a 10 kD PLAC (PL series Cellulose or polysulfone 0.93 square meter spiral cartridge (Millipore Australia Pty Ltd). The peptide containing solution is then subjected to tangental flow filtration for 6 hours by addition of purified water to the reservoir to dialysis off the small inorganic ions used for ion exchange procedure as well as peptides with molecular weights below the cut-off of the membrane. The retentate was then concentrated by diafiltration in the same apparatus, collected and water removed by freeze drying. In such a procedure the product obtained by this method was designated as INR-195 and was used for the rat CIA experiments described herein.

2. Biological Activity

Determination of Collagen or Collagen Peptide Content in Preparations by Assay for Hydroxyproline The collagen content of polypeptides separated by ion exchange was estimated by measuring the concentration of the amino acid hydroxyproline which is unique to this protein. Each freeze dried sample was directly dissolved in $H_2O$ (10 mg/ml) and then hydrolysed in 5 N HCl at 110° C. for 24 h. The hydrolysed sample solution was neutralised to pH 7 before dilution and analysis. The hydroxyproline concentration in these solutions was determined using the method of Stegman and Stalder (Stegman H and Stalder K. Determination of Hydroxyproline. Clin. Chim. Acta 18:267-273, 1967) by using a L-hydroxyproline standard and measuring the absorbance at 562 nm after the addition of chloramine T and p-dimethylaminobenzaldehyde to develop the chromophore. The hydroxyproline concentration was multiplied by 7.4 to give an estimate of the collagen content.

Determination of Protein Content of Preparations Content by the Bicinchoninic Acid (BCA) Assay The total protein content of polypeptide samples was determined using BCA assay (Smith P K, Krohn R I, Hermanson G T, Mallia A K, Gartner F H, Provenzano M D, Fujimoto E K, Goeke N M, Olson B J and Klenk D C. Anal. Biochem. 150, 76-85, 1985). Freeze dried polypeptide samples were directly dissolved in $H_2O$ to provide a 2.0 mg/ml solution and 20 µl of each sample solution was added to a well of 96-well plates. Just prior to assay, 50 parts of reagent 1 (0.4% NaOH; 1.7% $Na_2CO_3$; 0.95% $NaHCO_3$; 1.0% bicinchoninic acid; 0.16% $Na_2$-tartrate) was mixed with reagent 2 (4% $CuSO_4.5H_2O$). Two hundred micro liters of this working reagent was added to the sample solution. After incubation at 37° C. for 60 min the absorbance $A_{562}$ was read using a Thermomax microplate reader. Bovine serum albumin (BSA) or highly purified gelatine (Gibco) at 0-10 µg/well were used to construct a standard curve.

Analysis of Polypeptides Separated by Ion Exchange Using SDS-Polyacrylamide Gel Electrophoresis (SDS-PAGE)

Freeze dried polypeptide samples were dissolved in $H_2O$ and then mixed 1:1 with 2× sample loading buffer (0.07 M TrisHCl, 1.5% SDS, 20% glycerol, 0.2M DTT and 0.1% BPB) to achieve the final concentrations of 4.0-20 mg/ml. The samples were boiled in a water bath for 5 min. 20 µl of above samples were loaded into the wells of 8-16% pre-cast Tris-glycine gel (Norvex). SeeBlue pre-stained low molecular weight range protein markers (Norvex) were loaded into wells on the left-hand side of the gel and electrophoresis was performed at 125 V for 2 h. The gel was stained in Coomassie blue 8250 solution (40% ethanol, 10% acetic acid and 0.2% Coomassie 8250) for 30 min and destained in a solution containing 10% ethanol and 7.5% acetic acid for 16 h. The gel was dried in a Bio-Rad Gelair drier.

SDS-PAGE of the polypeptides separated from the GAG-peptides by the ion exchange procedure showed the presence of a number of bands the most abundant of which had molecular weights of 36 kDaltons or less (FIG. 2).

Analysis of Polypeptides Separated by Ion Exchange Using Two-Dimensional Gradient SDS-PAGE Freeze dried polypeptide samples (6.5 mg) were dissolved in $H_2O$ and sonicated. Samples were then centrifuged at 20,000 g for 10 minutes then were loaded via in-gel rehydration methods for Isoelectric Focusing (IEF) using 11 cm gradient strips over a pH of 3-10. First Dimension focusing was at 35,000 Vh. The second dimension used separating gradient 8-18% T criterion format polyacrylamide slab gels. This second dimension electrophoresis was run at 1 hour @ 5 mA/gel and 4 hours @ 15 mA/gel. Gels were stained using SYPRO Ruby fluorescent stain then scanned to produce a digital image.

Two dimensional electrophoresis of the polypeptides separated from the GAG-peptides by the ion exchange procedure revealed the presence of at least 21 polypeptides (FIG. 4).

Tryptic Digestion and Matrix Assisted Laser Desorption Ionisation (MALDI) Mass Spectrometry Following two-dimensional gradient SDS-PAGE of samples they were subjected to an in gel 16 hour tryptic digest at 37° C. The resulting peptides were extracted from the gel with a 10% (v/v) acetonitrile, 1% (v/v) TFA solution. The samples were then cleaned up and concentrated using ZipTip. A 1 µL aliquot of each was spotted onto a sample plate with 1 µL of matrix (a-cyano-4-hydroxycinnamic acid, 8 mg/mL in 70% v/v AcN, 1% v/v TFA) and allowed to air dry. Matrix assisted laser desorption ionisation (MALDI) mass spectrometry was then performed with a Micromass Maldi Time of Flight Mass Spectrometer. A nitrogen laser (337 nm) was used to irradiate the sample. The spectra were acquired in reflectron mode in the mass range 750 to 3500 Da. A near point calibration was applied.

The peptide masses of the monoisotopic peak of the peptides from this analysis were searched against Bovine using ProteinLynx on MassLynx and Mammalia data bases using PeptIdent on Expasy.

Rat Collagen Induced Arthritis (CIA)

Two protocols, which are summarized in FIG. 5, were used to evaluate the anti-arthritic activities of the polypeptides isolated in this invention. The toleragenic protocol required that the polypeptides dissolved in water were given orally each day to Female Wistar rats (160-180 gm) 7 days before inducing the arthritis by the inoculation with 250 µg bovine tracheal type II collagen, given as 6 divided injections into their tailbase. In the therapeutic/prophylactic protocol the polypeptides were administered orally on the same day as the arthritis was induced in the animals and everyday thereafter.

The following signs of arthritis were assessed from Day 11 onwards but recorded for each experimental group on days 15 and 18 (see Tables 5 and 6 below).

Table 5 shows the results obtained for the anti-arthritic effects of the polypeptide fractions INR-126, INR-195 and the established anti-rheumatoid arthritis drug, aurothiomalate (ATM) using the rat CIA-prophylactic/therapeutic protocol. Note that INR-126 and INR-195 appear to show similar anti-arthritic activities at 20 mg/kg and are both superior to ATM in this animal model.

TABLE 5

Results demonstrating anti-arthritic activity of the polypeptides INR-195 and INR-126 relative to ATM in the Rat CIA model using the Prophylactic/Therapeutic protocol (15 days treatment)

| Rx n = 4 | Dose mg/kg | Mean arthritis scores Day 13 | Day 15 | Day 18 | Signs of arthritis Day 15 R/paw swell (mm) | F/paw swell (mm) | Weight change (g) | Signs of arthritis Day 18 R/paw swell (mm) | F/paw swell (mm) | Weight change (g) |
|---|---|---|---|---|---|---|---|---|---|---|
| None | — | 0.7 | 1.5 | 1.8 | 0.7 | 2.1 | +40 | 0.8 | 2.0 | −04 |
| INR-126 | 20 (oral) | 0.2** | 0.8* | 1.3 | 0.4 | 1.3* | +47 | 0.7 | 2.0 | +06 |
| INR-126 | 200 (oral) | 0.2** | 0.5* | 1.7 | 0.1 | 0.1** | +58 | 0.8 | 2.3 | +04 |
| INR-195 | 20 (oral) | 0.2* | 0.7* | 1.8 | 0.2 | 0.1** | +45 | 0.7 | 2.0 | +09 |
| ATM | 6.3 (SC) | 0.8 | 2.1 | 2.1 | 0.7 | 2.5 | +47 | 0.8 | 3.2 | +04 |

ATM = Aurothiomalate,
SC = subcutaneously,
** = $p < 0.005$
* = $p < 0.05$ relative to none Table 6 shows the results obtained for the anti-arthritic effects of the polypeptide fractions INR-126, INR-195 using the rat CIA-toleragenic protocol. Note that the smaller MW fraction INR-126 appears to exhibit a more longer lasting toleragenic activity than the higher MW fraction, INR-195.

Table 7 identifies the polypeptides separated by the SDS-PAGE 2-D electrophoresis after tryptic digestion and MALDI-MS of the cleaved fragments determined by comparison with corresponding trypsin digestion fragments available in published databases.

TABLE 6

Results demonstrating the anti-arthritic activity of the polypeptides INR-195 and INR-126 in the Rat CIA model using the toleragenic protocol where preparations are given for 7 days before inducing arthritis

| Rx n = 4 | Dose mg/kg | Mean arthritis scores | | | Signs of arthritis Day 15 | | | Signs of arthritis Day 18 | | |
|---|---|---|---|---|---|---|---|---|---|---|
| | | Day 13 | Day 15 | Day 18 | R/paw swell (mm) | F/paw swell (mm) | Weight change (g) | R/paw swell (mm) | F/paw swell (mm) | Weight change (g) |
| None | — | 0.7 | 1.3 | 1.5 | 0.8 | 2.8 | +58 | 0.8 | 2.5 | −01 |
| INR-126 | 20 (oral) | 0.1** | 0.6* | 0.5** | 0.2* | 1.4* | +50 | 0.06** | 1.1* | +09 |
| INR-195 | 20 (oral) | 0.6 | 0.5* | 1.5 | 0.1* | 0.1* | +44 | 0.6 | 1.5 | +05 |

**= p < 0.005

*= p < 0.05 relative to no treatment group

Rear paw swelling, fore paw swelling (measured as the change in mm relative to non-arthritic controls) and an overall arthritis score (scored 0-4+) determined on the basis of overall inflammation and other signs of disease e.g. piloerection, diminished mobility, poor grooming etc were determined as described previously (Lu S et al, Different therapeutic and bystander effects by intranasal administration of homologous type II and type IX collagens on the collagen-induced arthritis and Pristane-induced arthritis in rats. Clin Immunol. 90:119-127, 1999).

Preparations of Stained Histological Sections of Rat Joints.

Following sacrifice of the experimental animals rear and front paw joints were removed surgically and immediately placed in neutral buffered formaldehyde and processed for preparation of H and E and toluidine blue stained histological sections as described previously (Smith M M, Numata Y and Ghosh P, Effects of calcium pentosan polysulfate on joint inflammation and pouch fluid levels of leukocytes, nitric oxide and interleukin-6 in a rat model of arthritis. Current Therapeutic Research, 60: 561-576, 1999).

3. Discussion

Positive identification of 17 of the polypeptides took account of the percentage of sequence coverage, how well the masses matched the significant peaks in the MS spectra, the number of missed cleavages (if missed cleavages were present their location in the sequence was critical) and how well the MW and pI of the identified protein match. These sequences and their % match with known proteins are shown in Table 7 below.

TABLE 7

1
Tentative
NCF1_BOVIN
Neutrophil cytosol factor 1
Molecular weight: 45346
Matches: 5
MOWSE Score: 1.6076937e+003
Likelihood: 1.96e+003
Coverage: 14.80%
Matching peptides:
MW Delta Start End Sequence
841.4657 −88.56 120 126 (K)VRPDD LK(L)
886.4760 −21.99 127 134 (K)LPTDS QVK(K)
886.4508 −50.37 283 291 (K)AGQDV AQAK(S)
* 1164.5822 0.02 328 336 (R)NSVRF MQQR(R)
1730.7934 −0.01 56 70 (K)EMFPI EAGDI NPENR(I)
1891.9197 23.26 170 188 (K)GSSSQ MALAT GDVVD VVEK(N)
OR
Tentative
ALBU_BOVIN
Bovine Serum Albumin
Molecular weight: 69294
Matches: 5
MOWSE Score: 7.6716406e+001
Likelihood: 1.88e+003
Coverage: 8.73%
Matching peptides:
MW Delta Start End Sequence
711.3664 59.75 29 34 (K)SEIAH R(F)
* 959.5400 −35.02 210 218 (R)EKVLA SSAR(Q)
* 1000.5818 −23.99 233 241 (R)ALKAW SVAR(L)
1385.6133 −28.71 286 297 (K)YICDN QDTIS SK(L)
* 1961.9404 26.67 139 155 (K)LKPDP NTLCD EFKAD EK(K)
2
Tentative
Score: 0.19, 6 matching peptides: P35445 (COMP_BOVIN)
pI: undefined, Mw: undefined
Cartilage oligomeric matrix protein (COMP) (Fragment). - Bos taurus

TABLE 7-continued (Bovine).
user mass matching [Delta] #MC modification positionpeptide
mass (ppm) mass
887.4908 887.4404 −56.88 0 Cys_PAM: 10 8-14 DNCPLVR
1181.5063 1181.4463 −50.84 0 2xCys_PAM 26-34 WGDACDNCR
1226.6927 1226.631 −50.35 1 Cys_PAM: 69 62-71 IRNPVDNCPK
1337.5306 1337.491 −29.64 0 Cys_PAM: 53 50-61 GDACDDDIDGDR
1370.707 1370.6369 −51.19 0 168-179 LVPNPGQEDMDR
1386.6544 1386.6318 −16.32 0 MSO: 177 168-179 LVPNPGQEDMDR
11.4% of sequence covered:
3
No Good Match
4
No Good Match
5
No Good Match
6
No Good Match
7
ALBU_BOVIN
Bovine Serum Albumin
Molecular weight: 69294
Matches: 11
MOWSE Score: 9.5664269e+006
Likelihood: 4.27e+003
Coverage: 17.96%
Matching peptides:
MW Delta Start End Sequence
926.4862 −137.94 161 167 (K)YLYEI AR(R)
1162.6234 −74.58 66 75 (K)LVNEL TEFAK(T)
1282.7033 −96.76 361 371 (R)HPEYA VSVLL R(L)
1304.7088 −90.40 402 412 (K)HLVDE PQNLI K(Q)
* 1438.8045 −82.02 360 371 (R)RHPEY AVSVL LR(L)
1478.7881 −92.19 421 433 (K)LGEYG FQNAL IVR(Y)
1510.8355 −83.71 438 451 (K)VPQVS TPTLV EVSR(S)
1566.7354 −87.40 347 359 (K)DAFLG SFLYE YSR(R)
* 1638.9304 −66.09 437 451 (R)KVPQV STPTL VEVSR(S)
1414.6802 −38.28 569 580 (K)TVMEN FVAFV DK(C)
+ Methionine Sulfoxide
1893.9294 −61.74 508 523 (R)RPCFS ALTPD ETYVP K(A)
+ Cysteine acrylamide
8
ALBU_BOVIN
Bovine Serum Albumin
Molecular weight: 69294
Matches: 13
MOWSE Score: 7.6034479e+007
Likelihood: 1.17e+004
Coverage: 21.42%
Matching peptides:
MW Delta Start End Sequence
926.4862 −72.22 161 167 (K)YLYEI AR(R)
1162.6234 −28.39 66 75 (K)LVNEL TEFAK(T)
1282.7033 −47.50 361 371 (R)HPEYA VSVLL R(L)
1304.7088 −31.77 402 412 (K)HLVDE PQNLI K(Q)
* 1438.8045 −39.49 360 371 (R)RHPEY AVSVL LR(L)
1478.7881 −32.08 421 433 (K)LGEYG FQNAL IVR(Y)
1510.8355 −19.52 438 451 (K)VPQVS TPTLV EVSR(S)
1518.7388 −25.79 139 151 (K)LKPDP NTLCD EFK(A)
1566.7354 −34.55 347 359 (K)DAFLG SFLYE YSR(R)
* 1638.9304 −19.36 437 451 (R)KVPQV STPTL VEVSR(S)
* 988.5488 24.47 221 228 (R)LRCAS IQK(F)
+ Cysteine acrylamide
1414.6802 8.58 569 580 (K)TVMEN FVAFV DK(C)
+ Methionine Sulfoxide
1893.9294 −10.63 508 523 (R)RPCFS ALTPD ETYVP K(A)
+ Cysteine acrylamide
9
NCF1_BOVIN
10
Q95L50
Type IX collagen alpha 1 chain
Molecular weight: 20907
Matches: 5
MOWSE Score: 3.7725965e+003
Likelihood: 5.46e+003
Coverage: 28.34%
Matching peptides:
MW Delta Start End Sequence
933.4668 −63.69 61 68 (K)LGNNV DFR(I)

TABLE 7-continued 1051.6390 −43.95 173 181 (R)IESLP IKPR(G)
2183.0687 42.58 73 90 (R)HLYPN GLPEE YSFLT TFR(M)
832.4476 −30.07 155 161 (K)IMIGV ER(S)
+ Methionine Sulfoxide
1282.5976 −22.54 162 172 (R)SSATL FVDCN R(I)
+ Cysteine acrylamide
11
ALBU_BOVIN
Bovine Serum Albumin
Molecular weight: 69294
Matches: 5
MOWSE Score: 1.1175735e+003
Likelihood: 7.26e+002
Coverage: 10.21%
Matching peptides:
MW Delta Start End Sequence
926.4862 −156.39 161 167 (K)YLYEI AR(R)
1282.7033 −36.27 361 371 (R)HPEYA VSVLL R(L)
1566.7354 −84.65 347 359 (K)DAFLG SFLYE YSR(R)
* 1887.9876 −6.32 89 105 (K)SLHTL FGDEL CKVAS LR(E)
1887.9195 −42.39 169 183 (R)HPYFY APELL YYANK(Y)
1790.7021 −70.93 267 280 (K)ECCHG DLLEC ADDR(A)
+ Cysteine acrylamide
+ Cysteine acrylamide
+ Cysteine acrylamide
12
ALBU_BOVIN
Bovine Serum Albumin
Molecular weight: 69294
Matches: 16
MOWSE Score: 3.5119435e+010
Likelihood: 1.04e+004
Coverage: 28.17%
Matching peptides:
MW Delta Start End Sequence
926.4862 −106.87 161 167 (K)YLYEI AR(R)
1282.7033 28.51 361 371 (R)HPEYA VSVLL R(L)
1304.7088 −33.76 402 412 (K)HLVDE PQNLI K(Q)
1478.7881 −58.18 421 433 (K)LGEYG FQNAL IVR(Y)
1510.8355 −34.08 438 451 (K)VPQVS TPTLV EVSR(S)
* 1638.9304 −30.89 437 451 (R)KVPQV STPTL VEVSR(S)
* 1737.8032 −39.00 387 401 (K)DDPHA CYSTV FDKLK(H)
1120.5223 −76.32 588 597 (K)EACFA VEGPK(L)
+ Cysteine acrylamide
1165.5220 −96.70 499 507 (K)CCTES LVNR(R)
+ Cysteine acrylamide
+ Cysteine acrylamide
1193.5169 −102.89 460 468 (R)CCTKP ESER(M)
+ Cysteine acrylamide
+ Cysteine acrylamide
1414.6802 16.07 569 580 (K)TVMEN FVAFV DK(C)
+ Methionine Sulfoxide
1567.6613 9.82 387 399 (K)DDPHA CYSTV FDK(L)
+ Cysteine acrylamide
1589.7759 24.36 139 151 (K)LKPDP NTLCD EFK(A)
+ Cysteine acrylamide
1753.8379 17.95 469 482 (R)MPCTE DYLSL ILNR(L)
+ Methionine Sulfoxide
+ Cysteine acrylamide
1893.9294 −3.13 508 523 (R)RPCFS ALTPD ETYVP K(A)
+ Cysteine acrylamide
1920.9291 10.74 529 544 (K)LFTFH ADICT LPDTE K(Q)
+ Cysteine acrylamide
13
Q95L50
Type IX collagen alpha 1 chain
Molecular weight: 20907
Matches: 9
MOWSE Score: 1.6928014e+007
Likelihood: 1.54e+004
Coverage: 62.03%
Matching peptides:
MW Delta Start End Sequence
816.4018 −95.42 124 130 (K)SVSFS YK(G)
816.4527 −32.98 155 161 (K)IMIGV ER(S)
933.4668 −51.91 61 68 (K)LGNNV DFR(I)
1051.6390 −49.75 173 181 (R)IESLP IKPR(G)
1570.7528 −9.01 99 111 (K)HWSIW QIQDS SGK(E)
2148.0739 −6.99 21 39 (R)IGQDD LPGFD LISQF QIDK(A)
2183.0687 −12.48 73 90 (R)HLYPN GLPEE YSFLT TFR(M)

TABLE 7-continued 2618.2765 −0.04 131 154 (K)GLDGS LQTAA FSNLP SLFDS QWHK(I)
832.4476 −3.52 155 161 (K)IMIGV ER(S)
+ Methionine Sulfoxide
1282.5976 −44.29 162 172 (R)SSATL FVDCN R(I)
+ Cysteine acrylamide
14
Q95L50
Type IX collagen alpha 1 chain
Molecular weight: 20907
Matches: 9
MOWSE Score: 1.6928014e+00
Likelihood: 8.48e+003
Coverage: 62.03%
Matching peptides:
MW Delta Start End Sequence
816.4018 −156.04 124 130 (K)SVSFS YK(G)
816.4527 −93.60 155 161 (K)IMIGV ER(S)
933.4668 −138.67 61 68 (K)LGNNV DFR(I)
1051.6390 −126.57 173 181 (R)IESLP IKPR(G)
1570.7528 −78.20 99 111 (K)HWSIW QIQDS SGK(E)
2148.0739 −53.45 21 39 (R)IGQDD LPGFD LISQF QIDK(A)
2183.0687 −61.45 73 90 (R)HLYPN GLPEE YSFLT TFR(M)
2618.2765 −0.10 131 154 (K)GLDGS LQTAA FSNLP SLFDS QWHK(I)
832.4476 −105.98 155 161 (K)IMIGV ER(S)
+ Methionine Sulfoxide
1282.5976 −119.59 162 172 (R)SSATL FVDCN R(I)
+ Cysteine acrylamide
15
Q95L50
Type IX collagen alpha 1 chain
Molecular weight: 20907
Matches: 7
MOWSE Score: 5.0424749e+005
Likelihood: 8.67e+003
Coverage: 48.13%
Matching peptides:
MW Delta Start End Sequence
816.4018 103.26 124 130 (K)SVSFS YK(G)
816.4527 165.71 155 161 (K)IMIGV ER(S)
933.4668 13.11 61 68 (K)LGNNV DFR(I)
1051.6390 5.50 173 181 (R)IESLP IKPR(G)
1570.7528 −0.05 99 111 (K)HWSIW QIQDS SGK(E)
2183.0687 −17.84 73 90 (R)HLYPN GLPEE YSFLT TFR(M)
2618.2765 0.11 131 154 (K)GLDGS LQTAA FSNLP SLFDS QWHK(I)
1282.5976 −29.95 162 172 (R)SSATL FVDCN R(I)
+ Cysteine acrylamide
16
Q95L50
Type IX collagen alpha 1 chain
Molecular weight: 20907
Matches: 5
MOWSE Score: 1.6468835e+004
Likelihood: 8.25e+003
Coverage: 34.76%
Matching peptides:
MW Delta Start End Sequence
933.4668 35.82 61 68 (K)LGNNV DFR(I)
1051.6390 30.60 173 181 (R)IESLP IKPR(G)
2148.0739 0.08 21 39 (R)IGQDD LPGFD LISQF QIDK(A)
2183.0687 −1.95 73 90 (R)HLYPN GLPEE YSFLT TFR(M)
1282.5976 −7.80 162 172 (R)SSATL FVDCN R(I)
+Cysteine acrylamide
17
Q95L50
Type IX collagen alpha 1 chain
Molecular weight: 20907
Matches: 8
MOWSE Score: 9.0085540e+005
Likelihood: 5.86e+003
Coverage: 49.20%
Matching peptides:
MW Delta Start End Sequence
816.4018 −137.06 124 130 (K)SVSFS YK(G)
816.4527 −74.62 155 161 (K)IMIGV ER(S)
933.4668 −125.07 61 68 (K)LGNNV DFR(I)
1051.6390 −117.92 173 181 (R)IESLP IKPR(G)
1570.7528 −50.26 99 111 (K)HWSIW QIQDS SGK(E)
2148.0739 −4.71 21 39 (R)IGQDD LPGFD LISQF QIDK(A)
2183.0687 −24.99 73 90 (R)HLYPN GLPEE YSFLT TFR(M)
832.4476 −86.04 155 161 (K)IMIGV ER(S)
+ Methionine Sulfoxide
1282.5976 −97.22 162 172 (R)SSATL FVDCN R(I)
+ Cysteine acrylamide
18
Q95L50
Type IX collagen alpha 1 chain
Molecular weight: 20907
Matches: 5
MOWSE Score: 1.6468835e+004
Likelihood: 2.56e+003
Coverage: 34.76%
Matching peptides:
MW Delta Start End Sequence
933.4668 −122.28 61 68 (K)LGNNV DFR(I)
1051.6390 −107.17 173 181 (R)IESLP IKPR(G)
2148.0739 0.02 21 39 (R)IGQDD LPGFD LISQF QIDK(A)
2183.0687 −6.21 73 90 (R)HLYPN GLPEE YSFLT TFR(M)
1282.5976 −90.21 162 172 (R)SSATL FVDCN R(I)
+ Cysteine acrylamide
19
OBP_BOVIN
Odorant-binding protein
Molecular weight: 18503
Matches: 7
MOWSE Score: 4.8550116e+005
Likelihood: 2.71e+004
Coverage: 50.94%
Matching peptides:
MW Delta Start End Sequence
959.4825 −4.49 30 37 (K)IQENG PFR(T)
993.4655 32.50 42 49 (R)ELVFD DEK(G)
1161.5706 1.66 50 59 (K)GTVDF YFSVK(R)
1207.6085 18.62 19 29 (R)TVYIG STNPE K(I)
1359.7259 −11.18 97 108 (R)THLVA HNINV DK(H)
1788.8067 1.86 145 159 (K)NVVNF LENED HPHPE(—)
1947.8486 2.44 74 90 (K)QDDGT YVADY EGQNV FK(I)
20
Q95L50
Type IX collagen alpha 1 chain
Molecular weight: 20907
Matches: 8
MOWSE Score: 9.0085540e+005
Likelihood: 6.84e+003
Coverage: 49.20%
Matching peptides:
MW Delta Start End Sequence
816.4018 −121.38 124 130 (K)SVSFS YK(G)
816.4527 −58.95 155 161 (K)IMIGV ER(S)
933.4668 −106.00 61 68 (K)LGNNV DFR(I)
1051.6390 −108.98 173 181 (R)IESLP IKPR(G)
1570.7528 −54.97 99 111 (K)HWSIW QIQDS SGK(E)
2148.0739 −18.35 21 39 (R)IGQDD LPGFD LISQF QIDK(A)
2183.0687 −25.77 73 90 (R)HLYPN GLPEE YSFLT TFR(M)
832.4476 −81.84 155 161 (K)IMIGV ER(S)
+ Methionine Sulfoxide
1282.5976 −93.79 162 172 (R)SSATL FVDCN R(I)
+ Cysteine acrylamide
21
Q95L50
Type IX collagen alpha 1 chain
Molecular weight: 20907
Matches: 8
MOWSE Score: 9.0085540e+005
Likelihood: 6.26e+003
Coverage: 49.20%
Matching peptides:
MW Delta Start End Sequence
816.4018 −133.87 124 130 (K)SVSFS YK(G)
816.4527 −71.44 155 161 (K)IMIGV ER(S)
933.4668 −113.93 61 68 (K)LGNNV DFR(I)
1051.6390 −115.35 173 181 (R)IESLP IKPR(G)
1570.7528 −60.83 99 111 (K)HWSIW QIQDS SGK(E)
2148.0739 −9.04 21 39 (R)IGQDD LPGFD LISQF QIDK(A)
2183.0687 −23.66 73 90 (R)HLYPN GLPEE YSFLT TFR(M)
832.4476 −68.62 155 161 (K)IMIGV ER(S)
+ Methionine Sulfoxide
1282.5976 −93.25 162 172 (R)SSATL FVDCN R(I)
+ Cysteine acrylamide The most abundant polypeptide fragments present in those isolated from CaP by the ion exchange method were derived from the NC4 domain of the type IX collagen a 1 chain [Molecular weight: 27,139 Da, (Vasios G, Nishimura I, Konomi H, van der Rest M, Cartilage Type IX collagen-proteoglycan contains a large amino-terminal globular domain encoded by multiple exons. J Biol Chem 263: 2324-2329, 1988)]. This is evident by combining the sequences obtained from the trypsin generated products shown in Table 7 for: Polypeptide 10, Polypeptide 13, Polypeptide 14, Polypeptide 15, Polypeptide 16, Polypeptide 17, Polypeptide 18, Polypeptide 20 and Polypeptide 21 and super-imposing them on part of the bovine NC4 domain of the α1(IX) chain as shown in Table 8 below. This conclusion is also supported by comparison of the observed peptide sequences with the published NC4 domain of the α1(IX) chain from chick sterna (Vasios G, Nishimura I, Konomi H, van der Rest M, Cartilage Type IX collagen-proteoglycan contains a large amino-terminal globular domain encoded by multiple exons. J Biol Chem 263: 2324-2329, 1988) and shown in Table 2. Furthermore the estimated molecular weights and isoelectric points of Polypeptide 13, Polypeptide 14, Polypeptide 15, Polypeptide 16, Polypeptide 17, and Polypeptide 18 shown in Table 1 are consistent with their origin as the NC4 domain of the α1(IX) chain which has a molecular weight of about 27,00 Da and isoelectric point of 9.7.

Table 8 show the partial amino acid sequence of the bovine NC4 domain of type IX collagen alpha 1 chain sequence obtained from the ExPASy TrEMBL database on which the peptide sequences obtained from the MALD-MS peptide mass fingerprinting of gel spot 13 (FIG. 4) has been superimposed as bolded type where they are identical.

the polypeptides from the ion-exchange supernatants is also supportive of the proteolytic cleavage of the NC4 domain of type IX collagen alpha 1 chain. COMP through its C-terminal domain is known to interact with the non-collagenous domains (NC1-4) of the type IX collagen alpha 1 chain and could be enzymatically processed when the NC4 domain is cleaved from the rest of the type IX collagen alpha-1 chain since theses two proteins are strongly associated and play key structural roles in the assembly of the extracellular matrix of cartilage. As already mentioned, the type IX collagen is located on the surface of the type II collagen fibrils where it serves as cross linking units between fibrils and itself. It was therefore surprising to find that none of the polypeptides isolated contain any peptides originating from the type II collagen molecule suggesting that the autolytic process is selective for the NC4 domain of the type IX collagen molecule.

Fragments of Bovine Serum Albumin (Molecular weight: 69294) (Polypeptide 7, Polypeptide 8, Polypeptide 9, Polypeptide 11, Polypeptide 12) were also found in the polypeptide fraction of CaP (Table 7). The presence of fragments of this protein was not unexpected in view of the large reservoir available in the blood of tissues adjacent to the tracheal cartilage.

Neutrophil cytosol factor 1 (Molecular weight: 45346) (Polypeptide 1 and Polypeptide 9), Odorant-binding protein

TABLE 8

```
         10          20          30          40          50          60
          |           |           |           |           |           |
PRFPVNSNSN GENELCPKVR IGQDDLPGFD LISQFQIDKA ASRRAIQRVV GSTALQVAYK 70          80          90         100         110         120
          |           |           |           |           |           |
LGNNVDFRIP TRHLYPNGLP EEYSFLTTFR MTGSTLEKHW SIWQIQDSSG KEQVGVKING 130         140         150         160         170         180
          |           |           |           |           |           |
QTKSVSFSYK GLDGDLQTAA FSNLPSLFDS QWHKIMIGVE RSSATLFCDC NRIESLPIKP

RGQIDVD   (SEQ ID NO. 20)
```

Figure 1:
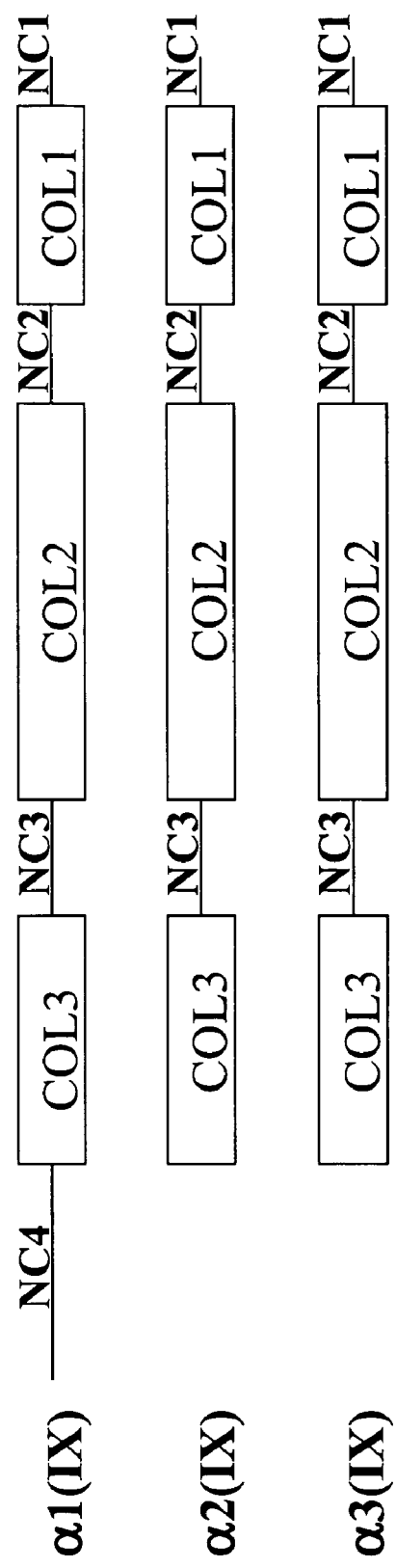

While the 4 non-collagenous domains (NC1, 2, 3 and 4, FIG. 1) along the type IX collagen α1 chain are known to be the most susceptible regions to proteolytic cleavage by a wide range of proteinases, the NC4 domain is the most venerable of these regions because of its physical extension beyond the COL3 domain and the rest of the alpha chain which together with the other 2 alpha chains lies on the surface of the type II collagen fibril. The results obtained previously also indicate that the endogenous cathepsin family of proteinases were largely responsible for the release of matrix peptides fragments from cartilage under the conditions described herein. Significantly, that the NC4 domain of type IX collagen alpha 1 chain is rich in Arginine residues which constitutes part of the preferred cleavage sites for the cathepsins (Maciewicz R A, Etherington D J. A comparison of four cathepsins (B, L, N and S) with collagenolytic activity from rabbit spleen, Biochem. J, 256: 433-4440, 1988).

The finding of a fragment (Polypeptide 2) of bovine cartilage oligomeric matrix protein (COMP) (peptides 2 and 3) in (Molecular weight: 18503) (Polypeptide 19) have not previously been reported to be present in cartilage and their functions, if any, are therefore unknown. Odorant-binding protein has however, been identified in bovine nasal mucosa endothelium which is physically close to the trachea. It is possible that this protein is sequestered to the tracheal cartilage and is not in fact a chondrocyte biosynthetic product. Since bovine odorant protein is not a cartilage derived antigen it would not be expected to be effective in the collagen induced arthritis model used to identify ant-arthritic activity in the present application.

Table 9(a) shows an amino acid sequence of cartilage oligomeric matrix protein (fragment)—bovine and 9(b) shows an amino acid sequence for oderant binding protein—bovine obtained from the ExPASy TrEMBL database on which the peptide sequences obtained from the peptide mass fingerprinting of gel spots 2 and 19 respectively have been superimposed as bolded type where they are identical.

TABLE 9a

Cartilage oligomeric matrix protein [Fragment] - bovine

```
         10         20         30         40         50         60
          |          |          |          |          |          |
DGVLNEKDNC PLVRNPQDRN TDGDKWGDAC DNCRSQKNDD QKDTDKDGRG DACDDDIDGD
         70         80         90        100        110        120
          |          |          |          |          |          |
RIRNPVDNCP KVPNSDQKDT DGDGCGDACD NCPQKSNADQ RDVDHDFVGD ACDSDQDQDG
        130        140        150        160        170        180
          |          |          |          |          |          |
DGHQDSKDNC PTVPNSAQQD SDHDGQGDAC DDDDDNDGVP DSRDNCRLVP NPGQEDMDRD
        190        200        210        220        230        240
          |          |          |          |          |          |
GVGDACQGDF DADKVVDKID VCPENEEVTL TDFRAFQTVV LDPEGDAQID PNWVVLNQGM
        250        260        270        280        290        300
          |          |          |          |          |          |
EIVQTMNSDP GLCVGYTAFN GVDFEGPFHV NTATFFFYAG FIFGYHHSSS FYVVMWKQME
        310        320        330        340        350        360
          |          |          |          |          |          |
QTYWQANPFR AVAEPQIQLK AVKSSTGPGE QLRNALWHTG DTASQVRLLW KDPRNVGWKD
        370        380        390        400        410        420
          |          |          |          |          |          |
KTSYRWFLQH RPQVGYIRVR FYEGPELVAD SNVILDTTMR GGRLGVFCFS QENIIWANLR
        430
          |
YRCNDTIPED YEAQRLLQA  (SEQ ID NO. 12)
```

TABLE 9b

Odorant-binding protein - bovine

```
         10         20         30         40         50         60
          |          |          |          |          |          |
AQEEEAEQNL SELSGPWRTV YIGSTNPEKI QENGPFRTYF RELVFDDEKG TVDFYFSVKR
         70         80         90        100        110        120
          |          |          |          |          |          |
DGKWKNVHVK ATKQDDGTYV ADYEGQNVFK IVSLSRTHLV AHNINVFKHG QTTELTELFV
        130        140        150
          |          |          |
KLNVEDEDLE KFWKLTEDKG IDKKNVVNFL ENEDHPHPE  (SEQ ID NO. 13)
```

In this respect it was significant that the polypeptides retained by using a TFF membrane with a protein cut-off of >30,000 Da were in-active in the rat CIA model (data not shown). On the other hand those polypeptides obtained in the dialysate with molecular weights <30,000 Da (INR-126 and INR-195) were active both active as tolerants and prophylactic anti-arthritic agents (FIGS. 6-7 and Tables 5-6). Furthermore, since the anti-arthritic activity of INR-126 (MW range 1000 Da-30,000 Da) appeared to be only slightly more active as a toleragen in the CIA model than INR-195 (MW range 10,000 Da-30,000 Da) it may be deduced that the majority of the ant-arthritic activity resides in polypeptides within the MW range of 10,000-30,000 Da which corresponds to peptides 11, 12, 13, 14, 15, 16, 17, 18, 20, 21 (Table 1).

The NC4 domain of the α1 (IX) chain or fragments derived from it have not previously been reported to exhibit anti-arthritic activity.

---

The invention claimed is:

1. A composition for treating or preventing arthritis or other degenerative disease, said composition comprising one or more polypeptides having at least 80% amino acid identity to SEQ ID NO: 14 and having an amino acid length of less than 250 amino acids in combination with a physiological acceptable carrier, wherein the polypeptide comprises one or more polypeptide fragments selected from:

(a) KSVSFSYKG (SEQ ID NO: 2);
   (b) KIMIGVERS (SEQ ID NO: 3);
   (c) RIESLPIKPRG (SEQ ID NO: 5);
   (d) KHWSIWQIQDSSGKE (SEQ ID NO: 6);
   (e) RIGQDDLPGFDLISQFQIDKA (SEQ ID NO: 7);
   (f) RHLYPNGLPEEYSFLTTFRM (SEQ ID NO: 8);
   (g) KGLDGSLQTAAFSNLPSLFDSQWHKI (SEQ ID NO: 9);
   (h) RSSATLFVDCNRI [SEQ ID NO: 11]; and
   (i) KLGNNVDFRI (SEQ ID NO: 4).

2. The composition of claim 1, wherein the polypeptide has a molecular weight of:
   a) less than 30,000 Da, or
   b) less than 30,000 Da and greater than or equal to 10,000 Da.

3. The composition of claim 1, wherein the polypeptide has identity to SEQ ID NO: 14 that is:
   a) at least 85%;
   b) at least 90%; or
   c) 100%.

4. The composition of claim 1, wherein the polypeptide comprises a fragment selected from:
   (a) residues 1-245 of SEQ ID NO:14;
   (b) residues 6-245 of SEQ ID NO:14;
   (c) residues 6-192 of SEQ ID NO:14;
   (d) residues 6-186 of SEQ ID NO:14;
   (e) residues 6-185 of SEQ ID NO:14;
   (f) residues 6-73 of SEQ ID NO:14; and
   (g) residues 85-185 of SEQ ID NO:14.

5. A method of inducing tolerance to at least one antigenic component of cartilage in an individual, the method comprising administering to the individual the composition of claim 1, wherein said administering induces said tolerance.

6. The method of claim 5, wherein the administered composition comprises one or more polypeptide fragment having a molecular weight of:
   a) less than 30,000 Da, or
   b) less than 30,000 Da and greater than or equal to 10,000 Da.

7. The method of claim 5, wherein the administered composition comprises one or more polypeptide fragment having identity to SEQ ID NO: 14 that is:
   a) at least 85%;
   b) at least 90%; or
   c) 100%.

8. The method of claim 5, wherein the composition comprises a polypeptide comprising a fragment selected from:

(a) residues 1-245 of SEQ ID NO:14;
(b) residues 6-245 of SEQ ID NO:14;
(c) residues 6-192 of SEQ ID NO:14;
(d) residues 6-186 of SEQ ID NO:14;
(e) residues 6-185 of SEQ ID NO:14;
(f) residues 6-73 of SEQ ID NO:14; and
(g) residues 85-185 of SEQ ID NO:14.

9. The method of claim 5, wherein the individual is a naive individual.

10. The method of claim 5, wherein said administering treats or prevents a degenerative condition.

11. The method of claim 10, wherein the degenerative condition or disease is arthritis or a musculoskeletal degenerative condition.

12. The method of claim 11, wherein the degenerative condition or disease is rheumatoid arthritis, osteoarthritis, disc degeneration, or osteoporosis.

13. The method of claim 10, wherein the administered composition comprises one or more polypeptide fragment having a molecular weight of:
   a) less than 30,000 Da, or
   b) less than 30,000 Da and greater than or equal to 10,000 Da.

14. The method of claim 10, wherein the administered composition comprises one or more polypeptide fragment having identity to SEQ ID NO: 14 that is:
   a) at least 85%;
   b) at least 90%; or
   c) 100%.

15. The method of claim 10, wherein the composition comprises a polypeptide comprising a fragment selected from:
   (a) residues 1-245 of SEQ ID NO:14;
   (b) residues 6-245 of SEQ ID NO:14;
   (c) residues 6-192 of SEQ ID NO:14;
   (d) residues 6-186 of SEQ ID NO:14;
   (e) residues 6-185 of SEQ ID NO:14;
   (g) residues 6-73 of SEQ ID NO:14; and
   (g) residues 85-185 of SEQ ID NO:14.

16. The method of claim 10, wherein the individual is a naive individual.

17. The method of claim 5, wherein said administering treats or prevents an autoimmune response in the individual to at least one antigenic component of cartilage.

18. The method of claim 17, wherein the administered composition comprises one or more polypeptide fragment having a molecular weight of:
   a) less than 30,000 Da, or
   b) less than 30,000 Da and greater than or equal to 10,000 Da.

19. The method of claim 17, wherein the administered composition comprises one or more polypeptide fragment having identity to SEQ ID NO: 14 that is:
   a) at least 85%;
   b) at least 90%; or
   c) 100%.

20. The method of claim 17, wherein the administered composition comprises a polypeptide comprising a fragment selected from:
   (a) residues 1-245 of SEQ ID NO:14;
   (b) residues 6-245 of SEQ ID NO:14;
   (c) residues 6-192 of SEQ ID NO:14;
   (d) residues 6-186 of SEQ ID NO:14;
   (e) residues 6-185 of SEQ ID NO:14;
   (f) residues 6-73 of SEQ ID NO:14; and
   (g) residues 85-185 of SEQ ID NO:14.

21. The method of claim 10, wherein said administering induces cartilage formation in the individual.

22. The method of claim 21, wherein the administered composition comprises one or more polypeptide fragment having a molecular weight of:
   a) less than 30,000 Da, or
   b) less than 30,000 Da and greater than or equal to 10,000 Da.

23. The method of claim 21, wherein the administered composition comprises one or more polypeptide fragment having identity to SEQ ID NO: 14 that is:
   a) at least 85%;
   b) at least 90%; or
   c) 100%.

24. The method of claim 21, wherein the composition comprises a polypeptide comprising a fragment selected from:
   (a) residues 1-245 of SEQ ID NO:14;
   (b) residues 6-245 of SEQ ID NO:14;
   (c) residues 6-192 of SEQ ID NO:14;
   (d) residues 6-186 of SEQ ID NO:14;
   (e) residues 6-185 of SEQ ID NO:14;
   (f) residues 6-73 of SEQ ID NO:14; and
   (g) residues 85-185 of SEQ ID NO:14.

* * * * *

SEQUENCE LISTING

```
<160> NUMBER OF SEQ ID NOS: 20

<210> SEQ ID NO 1
<211> LENGTH: 178
<212> TYPE: PRT
<213> ORGANISM: Artificial Sequence
<220> FEATURE:
<223> OTHER INFORMATION: Partial sequence of bovine NC4 domain of Type
      IX collagen alpha 1 chain

<400> SEQUENCE: 1

Pro Arg Phe Pro Val Asn Ser Asn Ser Asn Gly Glu Asn Glu Leu Cys
1               5                   10                  15
```

```
Pro Lys Val Arg Ile Gly Gln Asp Asp Leu Pro Gly Phe Asp Leu Ile
            20                  25                  30

Ser Gln Phe Gln Ile Asp Lys Ala Ala Ser Arg Arg Ala Ile Gln Arg
        35                  40                  45

Val Val Gly Ser Thr Ala Leu Gln Val Ala Tyr Lys Leu Gly Asn Asn
    50                  55                  60

Val Asp Phe Arg Thr Arg His Leu Tyr Pro Asn Gly Leu Pro Glu Glu
65                  70                  75                  80

Tyr Ser Phe Leu Thr Thr Phe Arg Met Thr Gly Ser Thr Leu Gly Lys
                85                  90                  95

His Trp Ser Ile Trp Gln Ile Gln Asp Ser Ser Gly Lys Glu Gln Val
            100                 105                 110

Gly Val Lys Ile Asn Gly Gln Thr Lys Ser Val Ser Phe Ser Tyr Lys
        115                 120                 125

Gly Leu Asp Gly Ser Leu Gln Thr Ala Ala Phe Ser Asn Leu Pro Ser
    130                 135                 140

Leu Phe Asp Ser Gln Trp His Lys Ile Met Ile Gly Val Glu Arg Ser
145                 150                 155                 160

Ser Ala Thr Leu Phe Val Asp Cys Asn Arg Ile Glu Ser Leu Pro Ile
                165                 170                 175

Lys Pro

<210> SEQ ID NO 2
<211> LENGTH: 9
<212> TYPE: PRT
<213> ORGANISM: Artificial Sequence
<220> FEATURE:
<223> OTHER INFORMATION: Type IX collagen alpha 1 chain peptide

<400> SEQUENCE: 2

Lys Ser Val Ser Phe Ser Tyr Lys Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Type IX collagen alpha 1 chain peptide

<400> SEQUENCE: 3

Lys Ile Met Ile Gly Val Glu Arg Ser
1               5

<210> SEQ ID NO 4
<211> LENGTH: 10
<212> TYPE: PRT
<213> ORGANISM: Artificial Sequence
<220> FEATURE:
<223> OTHER INFORMATION: Type IX collagen alpha 1 chain peptide

<400> SEQUENCE: 4

Lys Leu Gly Asn Asn Val Asp Phe Arg Ile
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Type IX collagen alpha 1 chain peptide
```

```
<400> SEQUENCE: 5

Arg Ile Glu Ser Leu Pro Ile Lys Pro Arg Gly
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Type IX collagen alpha 1 chain peptide

<400> SEQUENCE: 6

Lys His Trp Ser Ile Trp Gln Ile Gln Asp Ser Ser Gly Lys Glu
1               5                   10                  15

<210> SEQ ID NO 7
<211> LENGTH: 21
<212> TYPE: PRT
<213> ORGANISM: Artificial Sequence
<220> FEATURE:
<223> OTHER INFORMATION: Type IX collagen alpha 1 chain peptide

<400> SEQUENCE: 7

Arg Ile Gly Gln Asp Asp Leu Pro Gly Phe Asp Leu Ile Ser Gln Phe
1               5                   10                  15

Gln Ile Asp Lys Ala
            20

<210> SEQ ID NO 8
<211> LENGTH: 20
<212> TYPE: PRT
<213> ORGANISM: Artificial Sequence
<220> FEATURE:
<223> OTHER INFORMATION: Type IX collagen alpha 1 chain peptide

<400> SEQUENCE: 8

Arg His Leu Tyr Pro Asn Gly Leu Pro Glu Gly Tyr Ser Phe Leu Thr
1               5                   10                  15

Thr Phe Arg Met
            20

<210> SEQ ID NO 9
<211> LENGTH: 26
<212> TYPE: PRT
<213> ORGANISM: Artificial Sequence
<220> FEATURE:
<223> OTHER INFORMATION: Type IX collagen alpha 1 chain peptide

<400> SEQUENCE: 9

Lys Gly Leu Asp Gly Ser Leu Gln Thr Ala Ala Phe Ser Asn Leu Pro
1               5                   10                  15

Ser Leu Phe Asp Ser Gln Trp His Lys Ile
            20                  25

<210> SEQ ID NO 10
<211> LENGTH: 9
<212> TYPE: PRT
<213> ORGANISM: Artificial Sequence
<220> FEATURE:
<223> OTHER INFORMATION: Type IX collagen alpha 1 chain peptide

<400> SEQUENCE: 10

Lys Ile Met Ile Gly Val Glu Arg Ser
1               5
```

```
<210> SEQ ID NO 11
<211> LENGTH: 13
<212> TYPE: PRT
<213> ORGANISM: Artificial Sequence
<220> FEATURE:
<223> OTHER INFORMATION: Type IX collagen alpha 1 chain peptide

<400> SEQUENCE: 11

Arg Ser Ser Ala Thr Leu Phe Val Asp Cys Asn Arg Ile
1               5                  10

<210> SEQ ID NO 12
<211> LENGTH: 439
<212> TYPE: PRT
<213> ORGANISM: Artificial Sequence
<220> FEATURE:
<223> OTHER INFORMATION: Cartilage oligomeric matrix protein
      [Fragment] - bovine

<400> SEQUENCE: 12

Asp Gly Val Leu Asn Glu Lys Asp Asn Cys Pro Leu Val Arg Asn Pro
1               5                  10                  15

Asp Gln Arg Asn Thr Asp Gly Asp Lys Trp Gly Asp Ala Cys Asp Asn
            20                  25                  30

Cys Arg Ser Gln Lys Asn Asp Asp Gln Lys Asp Thr Asp Lys Asp Gly
        35                  40                  45

Arg Gly Asp Ala Cys Asp Asp Ile Asp Gly Asp Arg Ile Arg Asn
    50                  55                  60

Pro Val Asp Asn Cys Pro Lys Val Pro Asn Ser Asp Gln Lys Asp Thr
65                  70                  75                  80

Asp Gly Asp Gly Val Gly Asp Ala Cys Asp Asn Cys Pro Gln Lys Ser
                85                  90                  95

Asn Ala Asp Gln Arg Asp Val Asp His Asp Phe Val Gly Asp Ala Cys
            100                 105                 110

Asp Ser Asp Gln Asp Gln Asp Gly Asp Gly His Gln Ser Lys Asp
        115                 120                 125

Asn Cys Pro Thr Val Pro Asn Ser Ala Gln Gln Asp Ser Asp His Asp
    130                 135                 140

Gly Gln Gly Asp Ala Cys Asp Asp Asp Asp Asn Asp Gly Val Pro
145                 150                 155                 160

Asp Ser Arg Asp Asn Cys Arg Leu Val Pro Asn Pro Gly Gln Glu Asp
                165                 170                 175

Met Asp Arg Asp Gly Val Gly Asp Ala Cys Gln Gly Asp Phe Asp Ala
            180                 185                 190

Asp Lys Val Val Asp Lys Ile Asp Val Cys Pro Glu Asn Ala Glu Val
        195                 200                 205

Thr Leu Thr Asp Phe Arg Ala Phe Gln Thr Val Val Leu Asp Pro Glu
    210                 215                 220

Gly Asp Ala Gln Ile Asp Pro Asn Trp Val Val Leu Asn Gln Gly Met
225                 230                 235                 240

Glu Ile Val Gln Thr Met Asn Ser Asp Pro Gly Leu Cys Val Gly Tyr
                245                 250                 255

Thr Ala Phe Asn Gly Val Asp Phe Glu Gly Pro Phe His Val Asn Thr
            260                 265                 270

Ala Thr Asp Asp Asp Tyr Ala Gly Phe Ile Phe Gly Tyr His His Ser
        275                 280                 285

Ser Ser Phe Tyr Val Val Met Trp Lys Gln Met Glu Gln Thr Tyr Trp
    290                 295                 300
```

-continued

Gln Ala Asn Pro Phe Arg Ala Val Ala Glu Pro Gly Ile Gln Leu Lys
305                 310                 315                 320

Ala Val Lys Ser Ser Thr Gly Pro Gly Glu Gln Leu Arg Asn Ala Leu
            325                 330                 335

Trp His Thr Gly Asp Thr Ala Ser Gln Val Arg Leu Leu Trp Lys Asp
            340                 345                 350

Pro Arg Asn Val Gly Trp Lys Asp Lys Thr Ser Tyr Arg Trp Phe Leu
            355                 360                 365

Gln His Arg Pro Gln Val Gly Tyr Ile Arg Val Arg Phe Tyr Glu Gly
            370                 375                 380

Pro Glu Leu Val Ala Asp Ser Asn Val Ile Leu Asp Thr Thr Met Arg
385                 390                 395                 400

Gly Gly Arg Leu Gly Val Phe Cys Phe Ser Gln Glu Asn Ile Ile Trp
            405                 410                 415

Ala Asn Leu Arg Tyr Arg Cys Asn Asp Thr Ile Pro Glu Asp Tyr Glu
            420                 425                 430

Ala Gln Arg Leu Leu Gln Ala
            435

<210> SEQ ID NO 13
<211> LENGTH: 159
<212> TYPE: PRT
<213> ORGANISM: Artificial Sequence
<220> FEATURE:
<223> OTHER INFORMATION: Odorant-binding protein - bovine

<400> SEQUENCE: 13

Ala Gln Glu Glu Glu Ala Glu Gln Asn Leu Ser Glu Leu Ser Gly Pro
1               5                   10                  15

Trp Arg Thr Val Tyr Ile Gly Ser Thr Asn Pro Glu Lys Ile Gln Glu
            20                  25                  30

Asn Gly Pro Phe Arg Thr Tyr Phe Arg Glu Leu Val Phe Asp Asp Glu
            35                  40                  45

Lys Gly Thr Val Asp Phe Tyr Phe Ser Val Lys Arg Asp Gly Lys Trp
        50                  55                  60

Lys Asn Val His Val Lys Ala Thr Lys Gln Asp Asp Gly Thr Tyr Val
65                  70                  75                  80

Ala Asp Tyr Glu Gly Gln Asn Val Phe Lys Ile Val Ser Leu Ser Arg
                85                  90                  95

Thr His Leu Val Ala His Asn Ile Asn Val Asp Lys His Gly Gln Thr
            100                 105                 110

Thr Glu Leu Thr Glu Leu Phe Val Lys Leu Asn Val Glu Asp Glu Asp
            115                 120                 125

Leu Glu Lys Phe Trp Lys Leu Thr Glu Asp Lys Gly Ile Asp Lys Lys
        130                 135                 140

Asn Val Val Asn Phe Leu Glu Asn Glu Asp His Pro His Pro Glu
145                 150                 155

<210> SEQ ID NO 14
<211> LENGTH: 245
<212> TYPE: PRT
<213> ORGANISM: Artificial Sequence
<220> FEATURE:
<223> OTHER INFORMATION: human collagen type IX NC4 domain

<400> SEQUENCE: 14

Ala Val Lys Arg Arg Pro Arg Phe Pro Val Asn Ser Asn Ser Asn Gly
1               5                   10                  15

```
Gly Asn Glu Leu Cys Pro Lys Ile Arg Ile Gly Gln Asp Asp Leu Pro
             20                  25                  30

Gly Phe Asp Leu Ile Ser Gln Phe Gln Val Asp Lys Ala Ala Ser Arg
         35                  40                  45

Arg Ala Ile Gln Arg Val Val Gly Ser Ala Thr Leu Gln Val Ala Tyr
 50                  55                  60

Lys Leu Gly Asn Asn Val Asp Phe Arg Ile Pro Thr Arg Asn Leu Tyr
 65                  70                  75                  80

Pro Ser Gly Leu Pro Glu Glu Tyr Ser Phe Leu Thr Thr Phe Arg Met
             85                  90                  95

Thr Gly Ser Thr Leu Lys Lys Asn Trp Asn Ile Trp Gln Ile Gln Asp
            100                 105                 110

Ser Ser Gly Lys Glu Gln Val Gly Ile Lys Ile Asn Gly Gln Thr Gln
        115                 120                 125

Ser Val Val Phe Ser Tyr Lys Gly Leu Asp Gly Ser Leu Gln Thr Ala
    130                 135                 140

Ala Phe Ser Asn Leu Ser Ser Leu Phe Asp Ser Gln Trp His Lys Ile
145                 150                 155                 160

Met Ile Gly Val Glu Arg Ser Ser Ala Thr Leu Phe Val Asp Cys Asn
                165                 170                 175

Arg Ile Glu Ser Leu Pro Ile Lys Pro Arg Gly Pro Ile Asp Ile Asp
            180                 185                 190

Gly Phe Ala Val Leu Gly Lys Leu Ala Asp Asn Pro Gln Val Ser Val
        195                 200                 205

Pro Phe Glu Leu Gln Trp Met Leu Ile His Cys Asp Pro Leu Arg Pro
    210                 215                 220

Arg Arg Glu Thr Cys His Glu Leu Pro Ala Arg Ile Thr Pro Ser Gln
225                 230                 235                 240

Thr Thr Asp Glu Arg
                245

<210> SEQ ID NO 15
<211> LENGTH: 921
<212> TYPE: PRT
<213> ORGANISM: Artificial Sequence
<220> FEATURE:
<223> OTHER INFORMATION: human alpha (IX) chain precursor

<400> SEQUENCE: 15

Met Lys Thr Cys Trp Lys Ile Pro Val Phe Phe Val Cys Ser Phe
1               5                  10                  15

Leu Glu Pro Trp Ala Ser Ala Ala Val Lys Arg Arg Pro Arg Phe Pro
             20                  25                  30

Val Asn Ser Asn Ser Asn Gly Gly Asn Glu Leu Cys Pro Lys Ile Arg
         35                  40                  45

Ile Gly Gln Asp Asp Leu Pro Gly Phe Asp Leu Ile Ser Gln Phe Gln
 50                  55                  60

Val Asp Lys Ala Ala Ser Arg Arg Ala Ile Gln Arg Val Val Gly Ser
 65                  70                  75                  80

Ala Thr Leu Gln Val Ala Tyr Lys Leu Gly Asn Asn Val Asp Phe Arg
             85                  90                  95

Ile Pro Thr Arg Asn Leu Tyr Pro Ser Gly Leu Pro Glu Glu Tyr Ser
            100                 105                 110

Phe Leu Thr Thr Phe Arg Met Thr Gly Ser Thr Leu Lys Lys Asn Trp
        115                 120                 125

Asn Ile Trp Gln Ile Gln Asp Ser Ser Gly Lys Glu Gln Val Gly Ile
```

-continued

```
            130                 135                 140
Lys Ile Asn Gly Gln Thr Gln Ser Val Val Phe Ser Tyr Lys Gly Leu
145                 150                 155                 160

Asp Gly Ser Leu Gln Thr Ala Ala Phe Ser Asn Leu Ser Ser Leu Phe
                165                 170                 175

Asp Ser Gln Trp His Lys Ile Met Ile Gly Val Glu Arg Ser Ser Ala
            180                 185                 190

Thr Leu Phe Val Asp Cys Asn Arg Ile Glu Ser Leu Pro Ile Lys Pro
        195                 200                 205

Arg Gly Pro Ile Asp Ile Asp Gly Phe Ala Val Leu Gly Lys Leu Ala
    210                 215                 220

Asp Asn Pro Gln Val Ser Val Pro Phe Glu Leu Gln Trp Met Leu Ile
225                 230                 235                 240

His Cys Asp Pro Leu Arg Pro Arg Arg Glu Thr Cys His Glu Leu Pro
                245                 250                 255

Ala Arg Ile Thr Pro Ser Gln Thr Thr Asp Glu Arg Gly Pro Pro Gly
            260                 265                 270

Glu Gln Gly Pro Pro Gly Pro Pro Gly Pro Pro Gly Val Pro Gly Ile
        275                 280                 285

Asp Gly Ile Asp Gly Asp Arg Gly Pro Lys Gly Pro Pro Gly Pro Pro
    290                 295                 300

Gly Pro Ala Gly Glu Pro Gly Lys Pro Gly Ala Pro Gly Lys Pro Gly
305                 310                 315                 320

Thr Pro Gly Ala Asp Gly Leu Thr Gly Pro Asp Gly Ser Pro Gly Ser
                325                 330                 335

Ile Gly Ser Lys Gly Gln Lys Gly Glu Pro Gly Val Pro Gly Ser Arg
            340                 345                 350

Gly Phe Pro Gly Arg Gly Ile Pro Gly Pro Pro Gly Pro Pro Gly Thr
        355                 360                 365

Ala Gly Leu Pro Gly Glu Leu Gly Arg Val Gly Pro Val Gly Asp Pro
    370                 375                 380

Gly Arg Arg Gly Pro Pro Gly Pro Pro Gly Pro Pro Gly Pro Arg Gly
385                 390                 395                 400

Thr Ile Gly Phe His Asp Gly Asp Pro Leu Cys Pro Asn Ala Cys Pro
                405                 410                 415

Pro Gly Arg Ser Gly Tyr Pro Gly Leu Pro Gly Met Arg Gly His Lys
            420                 425                 430

Gly Ala Lys Gly Glu Ile Gly Glu Pro Gly Arg Gln Gly His Lys Gly
        435                 440                 445

Glu Glu Gly Asp Gln Gly Glu Leu Gly Glu Val Gly Ala Gln Gly Pro
    450                 455                 460

Pro Gly Ala Gln Gly Leu Arg Gly Ile Thr Gly Ile Val Gly Asp Lys
465                 470                 475                 480

Gly Glu Lys Gly Ala Arg Gly Leu Asp Gly Glu Pro Gly Pro Gln Gly
                485                 490                 495

Leu Pro Gly Ala Pro Gly Asp Gln Gly Gln Arg Gly Pro Pro Gly Glu
            500                 505                 510

Ala Gly Pro Lys Gly Asp Arg Gly Ala Glu Gly Ala Arg Gly Ile Pro
        515                 520                 525

Gly Leu Pro Gly Pro Lys Gly Asp Thr Gly Leu Pro Gly Val Asp Gly
    530                 535                 540

Arg Asp Gly Ile Pro Gly Met Pro Gly Thr Lys Gly Glu Pro Gly Lys
545                 550                 555                 560
```

```
Pro Gly Pro Pro Gly Asp Ala Gly Leu Gln Gly Leu Pro Gly Val Pro
            565                 570                 575

Gly Ile Pro Gly Ala Lys Gly Val Ala Gly Glu Lys Gly Ser Thr Gly
        580                 585                 590

Ala Pro Gly Lys Pro Gly Gln Met Gly Asn Ser Gly Lys Pro Gly Gln
    595                 600                 605

Gln Gly Pro Pro Gly Glu Val Gly Pro Arg Gly Pro Gln Gly Leu Pro
610                 615                 620

Gly Ser Arg Gly Glu Leu Gly Pro Val Gly Ser Pro Gly Leu Pro Gly
625                 630                 635                 640

Lys Leu Gly Ser Leu Gly Ser Pro Gly Leu Pro Gly Leu Pro Gly Pro
            645                 650                 655

Pro Gly Leu Pro Gly Met Lys Gly Asp Arg Gly Val Val Gly Glu Pro
        660                 665                 670

Gly Pro Lys Gly Glu Gln Gly Ala Ser Gly Glu Glu Gly Glu Ala Gly
    675                 680                 685

Glu Arg Gly Glu Leu Gly Asp Ile Gly Leu Pro Gly Pro Lys Gly Ser
    690                 695                 700

Ala Gly Asn Pro Gly Glu Pro Gly Leu Arg Gly Pro Glu Gly Ser Arg
705                 710                 715                 720

Gly Leu Pro Gly Val Glu Gly Pro Arg Gly Pro Pro Gly Pro Arg Gly
            725                 730                 735

Val Gln Gly Glu Gln Gly Ala Thr Gly Leu Pro Gly Val Gln Gly Pro
        740                 745                 750

Pro Gly Arg Ala Pro Thr Asp Gln His Ile Lys Gln Val Cys Met Arg
    755                 760                 765

Val Ile Gln Glu His Phe Ala Glu Met Ala Ala Ser Leu Lys Arg Pro
    770                 775                 780

Asp Ser Gly Ala Thr Gly Leu Pro Gly Arg Pro Gly Pro Pro Gly Pro
785                 790                 795                 800

Pro Gly Pro Pro Gly Glu Asn Gly Phe Pro Gly Gln Met Gly Ile Arg
            805                 810                 815

Gly Leu Pro Gly Ile Lys Gly Pro Pro Gly Ala Leu Gly Leu Arg Gly
        820                 825                 830

Pro Lys Gly Asp Leu Gly Glu Lys Gly Glu Arg Gly Pro Pro Gly Arg
    835                 840                 845

Gly Pro Asn Gly Leu Pro Gly Ala Ile Gly Leu Pro Gly Asp Pro Gly
850                 855                 860

Pro Ala Ser Tyr Gly Lys Asn Gly Arg Asp Gly Glu Arg Gly Pro Pro
865                 870                 875                 880

Gly Leu Ala Gly Ile Pro Gly Val Pro Gly Pro Pro Gly Pro Pro Gly
            885                 890                 895

Leu Pro Gly Phe Cys Glu Pro Ala Ser Cys Thr Met Gln Ala Gly Gln
        900                 905                 910

Arg Ala Phe Asn Lys Gly Pro Asp Pro
    915                 920

<210> SEQ ID NO 16
<211> LENGTH: 243
<212> TYPE: PRT
<213> ORGANISM: Artificial Sequence
<220> FEATURE:
<223> OTHER INFORMATION: chicken collagen type IX NC4 domain

<400> SEQUENCE: 16

Thr Tyr Gln Gln Gln Ser Arg Leu Pro Val Ile Leu Gly Ala Arg Gln
```

```
                    1               5              10              15
Arg Thr Asp Leu Cys Pro Thr Ile Arg Ile Gly Glu Asp Asp Leu Pro
                 20              25              30

Gly Phe Asp Leu Ile Ser Gln Phe Gln Ile Glu Lys Ala Ala Ser Gln
                 35              40              45

Gly Ile Val Gln Arg Val Val Gly Ser Thr Ala Leu Gln Val Ala Tyr
     50              55              60

Lys Leu Gly Pro Asn Val Asp Phe Arg Ile Pro Thr Ser Ala Ile Tyr
65              70              75              80

Ser Asn Gly Leu Pro Asp Glu Tyr Ser Phe Leu Thr Thr Phe Arg Met
                 85              90              95

Thr Gly Ala Thr Leu Gln Lys Tyr Trp Thr Ile Trp Gln Ile Gln Asp
                100             105             110

Ser Ser Gly Lys Glu Gln Val Gly Val Asn Leu Asn Gly Pro Met Lys
                115             120             125

Ser Val Glu Phe Ser Tyr Lys Gly Val Asp Gly Ser Leu Gln Thr Ala
                130             135             140

Ser Phe Leu His Leu Pro Phe Leu Phe Asp Ser Gln Trp His Lys Leu
145             150             155             160

Met Ile Ser Val Glu Thr Thr Ser Val Thr Leu Phe Ile Asp Cys Ile
                165             170             175

Lys Val Glu Thr Leu Asn Ile Lys Pro Lys Gly Lys Ile Ser Val Asp
                180             185             190

Gly Phe Ser Val Leu Gly Arg Leu Lys Asn Asn Pro Gln Ile Ser Val
                195             200             205

Pro Phe Glu Val Gln Trp Met Pro Ile His Cys Asp Pro Leu Arg Pro
                210             215             220

Gln Arg Glu Gly Cys Gly Glu Leu Pro Ala Arg Ile Ser Gln Thr Val
225             230             235             240

Ile Glu Arg

<210> SEQ ID NO 17
<211> LENGTH: 503
<212> TYPE: PRT
<213> ORGANISM: Artificial Sequence
<220> FEATURE:
<223> OTHER INFORMATION: chicken alpha (IX) chain precursor

<400> SEQUENCE: 17

Met Lys Ser Asn Trp Lys Ile Thr Ala Phe Leu Tyr Met Cys Ser Phe
1               5              10              15

Leu Gly Ser Phe Ile Ser Ala Thr Tyr Gln Gln Gln Ser Arg Leu Pro
                 20              25              30

Val Ile Leu Gly Ala Arg Gln Arg Thr Asp Leu Cys Pro Thr Ile Arg
                 35              40              45

Ile Gly Glu Asp Asp Leu Pro Gly Phe Asp Leu Ile Ser Gln Phe Gln
     50              55              60

Ile Glu Lys Ala Ala Ser Gln Gly Ile Val Gln Arg Val Val Gly Ser
65              70              75              80

Thr Ala Leu Gln Val Ala Tyr Lys Leu Gly Pro Asn Val Asp Phe Arg
                 85              90              95

Ile Pro Thr Ser Ala Ile Tyr Ser Asn Gly Leu Pro Asp Glu Tyr Ser
                100             105             110

Phe Leu Thr Thr Phe Arg Met Thr Gly Ala Thr Leu Gln Lys Tyr Trp
                115             120             125
```

Thr Ile Trp Gln Ile Gln Asp Ser Ser Gly Lys Glu Gln Val Gly Val
130                 135                 140

Asn Leu Asn Gly Pro Met Lys Ser Val Glu Phe Ser Tyr Lys Gly Val
145                 150                 155                 160

Asp Gly Ser Leu Gln Thr Ala Ser Phe Leu His Leu Pro Phe Leu Phe
                165                 170                 175

Asp Ser Gln Trp His Lys Leu Met Ile Ser Val Glu Thr Thr Ser Val
                180                 185                 190

Thr Leu Phe Ile Asp Cys Ile Lys Val Glu Thr Leu Asn Ile Lys Pro
            195                 200                 205

Lys Gly Lys Ile Ser Val Asp Gly Phe Ser Val Leu Gly Arg Leu Lys
210                 215                 220

Asn Asn Pro Gln Ile Ser Val Pro Phe Glu Val Gln Trp Met Pro Ile
225                 230                 235                 240

His Cys Asp Pro Leu Arg Pro Gln Arg Glu Gly Cys Gly Glu Leu Pro
                245                 250                 255

Ala Arg Ile Ser Gln Thr Val Ile Glu Arg Gly Leu Pro Gly Pro Pro
                260                 265                 270

Gly Pro Pro Gly Pro Pro Gly Pro Pro Gly Val Pro Gly Ile Asp Gly
            275                 280                 285

Ile Asp Gly Glu Arg Gly Pro Asn Gly Pro Pro Gly Pro Pro Gly Pro
290                 295                 300

Asp Gly Asp Ala Gly Lys Ala Gly Ser Pro Gly Leu Pro Gly Glu Pro
305                 310                 315                 320

Gly Ala Asp Gly Leu Thr Gly Pro Asp Gly Ser Pro Gly Ala Thr Gly
                325                 330                 335

Pro Lys Gly Gln Lys Gly Glu Pro Gly Pro Gly Ala Arg Gly Leu
                340                 345                 350

Pro Gly Lys Gly Leu Leu Gly Pro Gly Pro Ala Gly Ala Ala Gly
            355                 360                 365

Leu Pro Gly Glu Val Gly Arg Ala Gly Pro Gly Asp Pro Gly Lys
            370                 375                 380

Arg Gly Pro Pro Gly Pro Pro Gly Pro Pro Gly Pro Arg Gly Thr Ile
385                 390                 395                 400

Gly Leu Gln Asp Gly Asp Pro Leu Cys Pro Asn Ala Cys Pro Pro Gly
                405                 410                 415

Glu Ala Gly Glu Arg Gly Glu Arg Gly Phe Pro Gly Arg Gly Val Lys
                420                 425                 430

Gly Leu Pro Gly Pro Arg Gly Leu Pro Gly Glu Pro Gly Lys Pro Ser
            435                 440                 445

Tyr Gly Arg Glu Gly Arg Asp Gly Val Arg Gly Pro Pro Gly Val Ala
            450                 455                 460

Gly Gln Pro Gly Ile Pro Gly Pro Pro Gly Pro Pro Gly Pro Pro Gly
465                 470                 475                 480

Tyr Cys Glu Pro Ser Ser Cys Arg Met Gln Ala Gly Gln Arg Ala Ala
                485                 490                 495

Gly Lys Asn Met Lys Gly Pro
            500

<210> SEQ ID NO 18
<211> LENGTH: 245
<212> TYPE: PRT
<213> ORGANISM: Artificial Sequence
<220> FEATURE:
<223> OTHER INFORMATION: mouse collagen type IX NC4 domain -continued

<400> SEQUENCE: 18

```
Thr Leu Lys Arg Arg Ala Arg Phe Pro Ala Asn Ser Ile Ser Asn Gly
1               5                   10                  15

Gly Ser Glu Leu Cys Pro Lys Ile Arg Ile Gly Gln Asp Asp Leu Pro
            20                  25                  30

Gly Phe Asp Leu Ile Ser Gln Phe Gln Ile Glu Lys Ala Ala Ser Arg
        35                  40                  45

Arg Thr Ile Gln Arg Val Val Gly Ser Thr Ala Leu Gln Val Ala Tyr
    50                  55                  60

Lys Leu Gly Ser Asn Val Asp Phe Arg Ile Pro Thr Arg His Leu Tyr
65                  70                  75                  80

Pro Ser Gly Leu Pro Glu Glu Tyr Ser Phe Leu Thr Thr Phe Arg Met
                85                  90                  95

Thr Gly Ser Thr Leu Glu Lys His Trp Asn Ile Trp Gln Ile Gln Asp
            100                 105                 110

Ser Ala Gly Arg Glu Gln Val Gly Val Lys Ile Asn Gly Gln Thr Lys
        115                 120                 125

Ser Val Ala Phe Ser Tyr Lys Gly Leu Asp Gly Ser Leu Gln Thr Ala
    130                 135                 140

Ala Phe Leu Asn Leu Pro Ser Leu Phe Asp Ser Arg Trp His Lys Leu
145                 150                 155                 160

Met Ile Gly Val Glu Arg Thr Ser Ala Thr Leu Phe Ile Asp Cys Ile
                165                 170                 175

Arg Ile Glu Ser Leu Pro Ile Lys Pro Arg Gly Gln Ile Asp Ala Asp
            180                 185                 190

Gly Phe Ala Val Leu Gly Lys Leu Val Asp Asn Pro Gln Val Ser Val
        195                 200                 205

Pro Phe Glu Leu Gln Trp Met Leu Ile His Cys Asp Pro Leu Arg Pro
    210                 215                 220

Arg Arg Glu Thr Cys His Glu Leu Pro Ile Arg Ile Thr Thr Ser Gln
225                 230                 235                 240

Thr Thr Asp Glu Arg
                245
```

<210> SEQ ID NO 19
<211> LENGTH: 921
<212> TYPE: PRT
<213> ORGANISM: Artificial Sequence
<220> FEATURE:
<223> OTHER INFORMATION: mouse alpha (IX) chain precursor

<400> SEQUENCE: 19

```
Met Lys Asn Phe Trp Lys Ile Ser Val Phe Phe Cys Val Cys Ser Cys
1               5                   10                  15

Leu Gly Pro Trp Val Ser Ala Thr Leu Lys Arg Arg Ala Arg Phe Pro
            20                  25                  30

Ala Asn Ser Ile Ser Asn Gly Gly Ser Glu Leu Cys Pro Lys Ile Arg
        35                  40                  45

Ile Gly Gln Asp Asp Leu Pro Gly Phe Asp Leu Ile Ser Gln Phe Gln
    50                  55                  60

Ile Glu Lys Ala Ala Ser Arg Arg Thr Ile Gln Arg Val Val Gly Ser
65                  70                  75                  80

Thr Ala Leu Gln Val Ala Tyr Lys Leu Gly Ser Asn Val Asp Phe Arg
                85                  90                  95

Ile Pro Thr Arg His Leu Tyr Pro Ser Gly Leu Pro Glu Glu Tyr Ser
            100                 105                 110
```

```
Phe Leu Thr Thr Phe Arg Met Thr Gly Ser Thr Leu Glu Lys His Trp
            115                 120                 125
Asn Ile Trp Gln Ile Gln Asp Ser Ala Gly Arg Glu Gln Val Gly Val
        130                 135                 140
Lys Ile Asn Gly Gln Thr Lys Ser Val Ala Phe Ser Tyr Lys Gly Leu
145                 150                 155                 160
Asp Gly Ser Leu Gln Thr Ala Ala Phe Leu Asn Leu Pro Ser Leu Phe
                165                 170                 175
Asp Ser Arg Trp His Lys Leu Met Ile Gly Val Glu Arg Thr Ser Ala
            180                 185                 190
Thr Leu Phe Ile Asp Cys Ile Arg Ile Glu Ser Leu Pro Ile Lys Pro
        195                 200                 205
Arg Gly Gln Ile Asp Ala Asp Gly Phe Ala Val Leu Gly Lys Leu Val
210                 215                 220
Asp Asn Pro Gln Val Ser Val Pro Phe Glu Leu Gln Trp Met Leu Ile
225                 230                 235                 240
His Cys Asp Pro Leu Arg Pro Arg Arg Glu Thr Cys His Glu Leu Pro
                245                 250                 255
Ile Arg Ile Thr Thr Ser Gln Thr Thr Asp Glu Arg Gly Pro Pro Gly
            260                 265                 270
Glu Gln Gly Pro Pro Gly Pro Pro Gly Pro Pro Gly Val Pro Gly Ile
        275                 280                 285
Asp Gly Ile Asp Gly Asp Arg Gly Pro Lys Gly Pro Pro Gly Pro Pro
290                 295                 300
Gly Pro Pro Gly Asp Pro Gly Lys Pro Gly Ala Pro Gly Lys Pro Gly
305                 310                 315                 320
Thr Pro Gly Ala Asp Gly Leu Thr Gly Pro Asp Gly Ser Pro Gly Ser
                325                 330                 335
Val Gly Pro Arg Gly Gln Lys Gly Glu Pro Gly Val Pro Gly Ser Arg
            340                 345                 350
Gly Phe Pro Gly Arg Gly Ile Pro Gly Pro Pro Gly Pro Pro Gly Thr
        355                 360                 365
Thr Gly Leu Pro Gly Glu Leu Gly Arg Val Gly Pro Ile Gly Asp Pro
        370                 375                 380
Gly Lys Arg Gly Pro Pro Gly Pro Pro Gly Pro Pro Gly Pro Ser Gly
385                 390                 395                 400
Thr Ile Gly Phe His Asp Gly Asp Pro Leu Cys Pro Asn Ser Cys Pro
                405                 410                 415
Pro Gly Arg Ser Gly Tyr Pro Gly Leu Pro Gly Met Arg Gly His Lys
            420                 425                 430
Gly Ala Lys Gly Glu Ile Gly Glu Pro Gly Arg Gln Gly His Lys Gly
        435                 440                 445
Glu Glu Gly Asp Gln Gly Glu Leu Gly Glu Val Gly Ala Gln Gly Pro
450                 455                 460
Pro Gly Pro Gln Gly Leu Arg Gly Ile Thr Gly Ile Val Gly Asp Lys
465                 470                 475                 480
Gly Glu Lys Gly Ala Arg Gly Phe Asp Gly Glu Pro Gly Pro Gln Gly
                485                 490                 495
Ile Pro Gly Ala Ala Gly Asp Gln Gly Gln Arg Gly Pro Pro Gly Glu
            500                 505                 510
Thr Gly Pro Lys Gly Asp Arg Gly Ile Gln Gly Ser Arg Gly Ile Pro
        515                 520                 525
Gly Ser Pro Gly Pro Lys Gly Asp Thr Gly Leu Pro Gly Val Asp Gly
```

```
                    530             535             540
Arg Asp Gly Ile Pro Gly Met Pro Gly Thr Lys Gly Glu Ala Gly Lys
545                 550             555             560

Pro Gly Pro Pro Gly Asp Val Gly Leu Gln Gly Leu Pro Gly Val Pro
                565             570             575

Gly Ile Pro Gly Ala Lys Gly Val Ala Gly Glu Lys Gly Asn Thr Gly
            580             585             590

Ala Pro Gly Lys Pro Gly Gln Leu Gly Ser Ser Gly Lys Pro Gly Gln
        595             600             605

Gln Gly Pro Pro Gly Glu Val Gly Pro Arg Gly Arg Gly Leu Pro
    610             615             620

Gly Ser Arg Gly Pro Val Gly Pro Glu Gly Ser Pro Gly Ile Pro Gly
625             630             635             640

Lys Leu Gly Ser Val Gly Ser Pro Gly Leu Pro Gly Leu Pro Gly Pro
                645             650             655

Pro Gly Leu Pro Gly Met Lys Gly Asp Arg Gly Val Phe Gly Glu Pro
            660             665             670

Gly Pro Lys Gly Glu Gln Gly Ala Ser Gly Glu Glu Gly Glu Ala Gly
        675             680             685

Ala Arg Gly Asp Leu Gly Asp Met Gly Gln Pro Gly Pro Lys Gly Ser
690             695             700

Val Gly Asn Pro Gly Glu Pro Gly Leu Arg Gly Pro Glu Gly Ile Arg
705             710             715             720

Gly Leu Pro Gly Val Glu Gly Pro Arg Gly Pro Pro Gly Pro Arg Gly
                725             730             735

Met Gln Gly Glu Gln Gly Ala Thr Gly Leu Pro Gly Ile Gln Gly Pro
            740             745             750

Pro Gly Arg Ala Pro Thr Asp Gln His Ile Lys Gln Val Cys Met Arg
        755             760             765

Val Val Gln Glu His Phe Val Glu Met Ala Ala Ser Leu Lys Arg Pro
    770             775             780

Asp Thr Gly Ala Ser Gly Leu Pro Gly Arg Pro Gly Pro Pro Gly Pro
785             790             795             800

Pro Gly Pro Pro Gly Glu Asn Gly Phe Pro Gly Gln Met Gly Ile Arg
                805             810             815

Gly Leu Pro Gly Ile Lys Gly Pro Pro Gly Ala Leu Gly Leu Arg Gly
            820             825             830

Pro Lys Gly Asp Leu Gly Glu Lys Gly Glu Arg Gly Pro Pro Gly Arg
        835             840             845

Gly Pro Lys Gly Leu Pro Gly Ala Ile Gly Leu Pro Gly Asp Pro Gly
    850             855             860

Pro Ala Ser Tyr Gly Lys Asn Gly Arg Asp Gly Glu Gln Gly Pro Pro
865             870             875             880

Gly Val Ala Gly Ile Pro Gly Val Pro Gly Pro Pro Gly Pro Pro Gly
                885             890             895

Pro Pro Gly Phe Cys Glu Pro Ala Ser Cys Thr Leu Gln Ser Gly Gln
            900             905             910

Arg Ala Phe Ser Lys Gly Pro Asp Lys
        915             920

<210> SEQ ID NO 20
<211> LENGTH: 187
<212> TYPE: PRT
<213> ORGANISM: Artificial Sequence
<220> FEATURE:
```

```
<223> OTHER INFORMATION: Partial sequence of bovine NC4 domain of Type
      IX collagen alpha 1 chain

<400> SEQUENCE: 20

Pro Arg Phe Pro Val Asn Ser Asn Ser Asn Gly Glu Asn Glu Leu Cys
1               5                   10                  15

Pro Lys Val Arg Ile Gly Gln Asp Asp Leu Pro Gly Phe Asp Leu Ile
                20                  25                  30

Ser Gln Phe Gln Ile Asp Lys Ala Ala Ser Arg Arg Ala Ile Gln Arg
            35                  40                  45

Val Val Gly Ser Thr Ala Leu Gln Val Ala Tyr Lys Leu Gly Asn Asn
    50                  55                  60

Val Asp Phe Arg Ile Pro Thr Arg His Leu Tyr Pro Asn Gly Leu Pro
65                  70                  75                  80

Glu Glu Tyr Ser Phe Leu Thr Thr Phe Arg Met Thr Gly Ser Thr Leu
                85                  90                  95

Glu Lys His Trp Ser Ile Trp Gln Ile Gln Asp Ser Ser Gly Lys Glu
                100                 105                 110

Gln Val Gly Val Lys Ile Asn Gly Gln Thr Lys Ser Val Ser Phe Ser
            115                 120                 125

Tyr Lys Gly Leu Asp Gly Ser Leu Gln Thr Ala Ala Phe Ser Asn Leu
    130                 135                 140

Pro Ser Leu Phe Asp Ser Gln Trp His Lys Ile Met Ile Gly Val Glu
145                 150                 155                 160

Arg Ser Ser Ala Thr Leu Phe Val Asp Cys Asn Arg Ile Glu Ser Leu
                165                 170                 175

Pro Ile Lys Pro Arg Gly Gln Ile Asp Val Asp
                180                 185
```